(12) United States Patent
Morrissette et al.

(10) Patent No.: US 7,619,086 B2
(45) Date of Patent: Nov. 17, 2009

(54) HIV INTEGRASE INHIBITORS

(75) Inventors: Matthew M. Morrissette, Radnor, PA (US); Peter D. Williams, Harleysville, PA (US); John S. Wai, Harleysville, PA (US); Thorsten E. Fisher, Hatfield, PA (US); Terry A. Lyle, Lederach, PA (US)

(73) Assignee: Merck & Co., Inc., Rahway, NJ (US)

( * ) Notice: Subject to any disclaimer, the term of this patent is extended or adjusted under 35 U.S.C. 154(b) by 217 days.

(21) Appl. No.: 10/591,914

(22) PCT Filed: Mar. 4, 2005

(86) PCT No.: PCT/US2005/007106

§ 371 (c)(1), (2), (4) Date: Sep. 8, 2006

(87) PCT Pub. No.: WO2005/086700

PCT Pub. Date: Sep. 22, 2005

(65) Prior Publication Data

US 2008/0139579 A1 Jun. 12, 2008

Related U.S. Application Data

(60) Provisional application No. 60/551,440, filed on Mar. 9, 2004.

(51) Int. Cl.
*C07D 221/18* (2006.01)
*C07D 221/22* (2006.01)
*A01N 43/40* (2006.01)
*A61K 31/435* (2006.01)

(52) U.S. Cl. .......................... 546/26; 514/277
(58) Field of Classification Search ........................ None
See application file for complete search history.

(56) References Cited

U.S. PATENT DOCUMENTS

| | | |
|---|---|---|
| 6,262,055 B1 | 7/2001 | Young et al. |
| 6,306,891 B1 | 10/2001 | Selnick et al. |
| 6,380,249 B1 | 4/2002 | Young et al. |
| 6,841,558 B2 | 1/2005 | Anthony et al. |
| 6,919,351 B2 | 7/2005 | Anthony et al. |
| 6,921,759 B2 | 7/2005 | Anthony et al. |
| 7,109,186 B2 | 9/2006 | Walker et al. |
| 7,169,780 B2 | 1/2007 | Crescenzi et al. |
| 7,211,572 B2 | 5/2007 | Miyazaki et al. |
| 7,217,713 B2 | 5/2007 | Crescenzi et al. |
| 7,232,819 B2 | 6/2007 | Di Francesco et al. |
| 7,279,487 B2 | 10/2007 | Egbertson et al. |
| 7,435,734 B2 | 10/2008 | Crescenzi et al. |
| 7,459,452 B2 | 12/2008 | Di Francesco et al. |
| 2003/0055071 A1 | 3/2003 | Anthony et al. |
| 2003/0229079 A1 | 12/2003 | Payne et al. |
| 2004/0229909 A1 | 11/2004 | Kiyama et al. |
| 2005/0010048 A1 | 1/2005 | Zhuang et al. |
| 2007/0161639 A1 | 7/2007 | Jones et al. |
| 2007/0179196 A1 | 8/2007 | Han et al. |
| 2008/0009490 A1 | 1/2008 | Williams et al. |

FOREIGN PATENT DOCUMENTS

| | | |
|---|---|---|
| EP | 1422218 A1 | 5/2004 |
| WO | WO 01/00578 A1 | 1/2001 |
| WO | WO 02/30426 A1 | 4/2002 |
| WO | WO 02/36734 A2 | 5/2002 |
| WO | WO 02/055079 A2 | 7/2002 |
| WO | WO 03/035076 A1 | 5/2003 |
| WO | WO 03/035077 A1 | 5/2003 |
| WO | WO 03/062204 A1 | 7/2003 |
| WO | WO 2004/004657 A2 | 1/2004 |
| WO | WO 2005/087767 A1 | 9/2005 |
| WO | WO 2005/087768 A1 | 9/2005 |
| WO | WO 2006/121831 A2 | 11/2006 |

OTHER PUBLICATIONS

Dorwald F. A. (Side reactions in organic synthesis, 2005, Wiley, VCH, Weinheim, p. IX of Preface).*
Ratner, L., et al., "Complete Nucleotide Sequence of the AIDS Virus, HTLV-III", Nature, vol. 313, pp. 277-284, (1985).
Toh, H., et al., "Close Structural Resemblance Between Putative Polymerase of a Drosphila Transposable Genetic Element 17.6 and Pol Gene Product of Moloney Murine Leukemia Virus", EMBO Journal, vol. 4, No. 5, pp. 1267-1272, (1985).

(Continued)

*Primary Examiner*—Frederick Krass
*Assistant Examiner*—Marcos Sznaidman
(74) *Attorney, Agent, or Firm*—Kenneth R. Walton; Sheldon O. Heber

(57) ABSTRACT

Compounds of Formula I are inhibitors of HIV integrase and inhibitors of HIV replication:

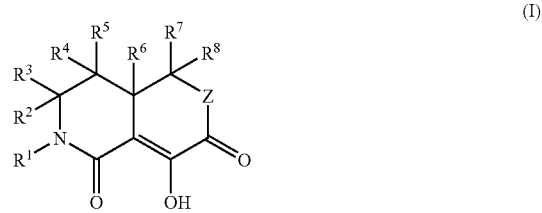

wherein Z, $R^1$, $R^2$, $R^3$, $R^4$, $R^5$, $R^6$, $R^7$, $R^8$ and $R^9$ are defined herein. The compounds are useful in the prevention and treatment of infection by HIV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines.

6 Claims, No Drawings

OTHER PUBLICATIONS

Power, M.D., et al., "Nucleotide Sequence of SRV-1, a Type D Simian Acquired Immune Deficiency Syndrome Retrovirus", Science, vol. 231, pp. 1567-1572, (1986).

Pearl, L.H., et al., "A Structural Model for the Retroviral Proteases", Nature, vol. 329, pp. 351-354, (1987).

Declaration of Interference No. 105,655 between (i) Jones et al., U.S. Appl. No. 10/587,601, filed Jul. 28, 2006, and (ii) Miyazaki et al., US 7,211,572.

Selected papers from Interference No. 105,655 between U.S. Appl. No. 10/587,601 (Merck) and US 7,211,572 (Japan Tobacco)—Merck Amended Miscellaneous Motion 1 dated Nov. 10, 2008; Interlocutory Order dated Nov. 18, 2008, Granting Merck's Unopposed Revised Miscellaneous Motion 1; Redeclaration of Interference dated Nov. 18, 2008; Judgement dated Dec. 5, 2008.

Preliminary Amendments filed Nov. 7, 2007 and Mar. 24, 2008 in U.S. Appl. No. 11/920,032 (unpublished national phase application of WO 2006/121831).

U.S. Appl. No. 12/316,027, filed Dec. 9, 2009, unpublished application.

Preliminary Amendment filed Dec. 9, 2008 in U.S. Appl. No. 12/316,027.

Second Preliminary Amendment filed Feb. 2, 2009 in U.S. Appl. No. 12/316,027.

\* cited by examiner

HIV INTEGRASE INHIBITORS

This application is the National Stage of International Application No. PCT/US2005/007106, filed on Mar. 4, 2005, which claims the benefit of U.S Provisional Application No. 60/551,440, filed Mar. 9, 2004, the disclosure of which is hereby incorporated by reference in its entirety.

FIELD OF THE INVENTION

The present invention is directed to hydroxy tetrahydronaphthyridine dione and hydroxy hexahydronaphthyridine dione compounds and hydroxy dihydropyranopyridine dione and hydroxytetrahydropyranopyridine dione compounds and pharmaceutically acceptable salts thereof, their synthesis, and their use as inhibitors of the HIV integrase enzyme. The compounds and pharmaceutically acceptable salts thereof of the present invention are useful for preventing or treating infection by HIV and for preventing or treating or delaying the onset of AIDS.

BACKGROUND OF THE INVENTION

A retrovirus designated human immunodeficiency virus (HIV), particularly the strains known as HIV type-1 (HIV-1) and type-2 (HIV-2) viruses, is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication. The inhibition of integrase in vitro and of HIV replication in cells is a direct result of inhibiting the strand transfer reaction catalyzed by the recombinant integrase in vitro in HIV infected cells. The particular advantage of the present invention is highly specific inhibition of HIV integrase and HIV replication.

The following references are of interest as background:

U.S. Pat. No. 6,380,249, U.S. Pat. No. 6,306,891, and U.S. Pat. No. 6,262,055 disclose 2,4-dioxobutyric acids and acid esters useful as HIV integrase inhibitors.

WO 01/00578 discloses 1-(aromatic- or heteroaromatic-substituted)-3-(heteroaromatic substituted)-1,3-propanediones useful as HIV integrase inhibitors.

US 2003/0055071 (corresponding to WO 02/30930), WO 02/30426, and WO 02/55079 each disclose certain 8-hydroxy-1,6-naphthyridine-7-carboxamides as HIV integrase inhibitors.

WO 02/036734 discloses certain aza- and polyaza-naphthalenyl ketones to be HIV integrase inhibitors.

WO 03/016275 discloses certain compounds having integrase inhibitory activity.

WO 03/35076 discloses certain 5,6-dihydroxypyrimidine-4-carboxamides as HIV integrase inhibitors, and WO 03/35077 discloses certain N-substituted 5-hydroxy-6-oxo-1,6-dihydropyrimidine-4-carboxamides as HIV integrase inhibitors.

WO 03/062204 discloses certain hydroxynaphthyridinone carboxamides that are useful as HIV integrase inhibitors.

WO 04/004657 discloses certain hydroxypyrrole derivatives that are HIV integrase inhibitors.

SUMMARY OF THE INVENTION

The present invention is directed to hydroxy polyhydronaphthyridine dione compounds and hydroxy polyhydropyranopyridine dione compounds. These compounds are useful in the inhibition of HIV integrase, the prevention of infection by HIV, the treatment of infection by HIV and in the prevention, treatment, and delay in the onset of AIDS and/or ARC, either as compounds or their pharmaceutically acceptable salts or hydrates (when appropriate), or as pharmaceutical composition ingredients, whether or not in combination with other HIV/AIDS antivirals, anti-infectives, immunomodulators, antibiotics or vaccines. More particularly, the present invention includes compounds of Formula I, and pharmaceutically acceptable salts thereof:

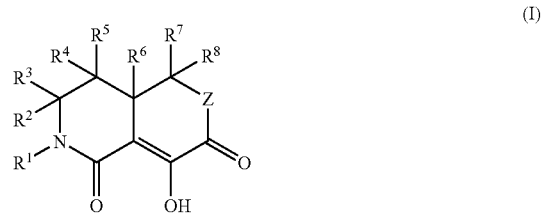

(I)

wherein:

Z is O or N—$R^9$;

$R^1$ is —$C_{1-6}$ alkyl substituted with $R^J$, wherein $R^J$ is:
  (A) aryl or aryl fused to a 5- or 6-membered heteroaromatic ring containing from 1 to 4 heteroatoms independently selected from N, O and S, wherein the aryl or fused aryl is
    (i) optionally substituted with from 1 to 5 substituents each of which is independently:
      (1) —$C_{1-6}$ alkyl, which is optionally substituted with —OH, —O—$C_{1-6}$ alkyl, —O—$C_{1-6}$ haloalkyl, —CN, —$NO_2$, —N($R^A$)$R^B$, —C(=O)N($R^A$)$R^B$, —C(=O)$R^A$, —$CO_2R^A$, —S(O)$_n R^A$, —$SO_2$N($R^A$)$R^B$, —N($R^A$)C(=O)$R^B$, —N($R^A$)$CO_2R^B$, —N($R^A$)$SO_2R^B$, —N($R^A$)$SO_2$N($R^A$)$R^B$, —OC(=O)N($R^A$)$R^B$, or —N($R^A$)C(=O)N($R^A$)$R^B$,
      (2) —O—$C_{1-6}$ alkyl,
      (3) —$C_{1-6}$ haloalkyl,
      (4) —O—$C_{1-6}$ haloalkyl,
      (5) —OH,
      (6) halo,
      (7) —CN, (8) —$NO_2$,
(9) —$N(R^A)R^B$,
(10) —$C(=O)N(R^A)R^B$,
(11) —$C(=O)R^A$,
(12) —$CO_2R^A$,
(13) —$SR^A$,
(14) —$S(=O)R^A$,
(15) —$SO_2R^A$,
(16) —$SO_2N(R^A)R^B$,
(17) —$N(R^A)SO_2R^B$,
(18) —$N(R^A)SO_2N(R^A)R^B$,
(19) —$N(R^A)C(=O)R^B$,
(20) —$N(R^A)C(=O)—C(=O)N(R^A)R^B$, or
(21) —$N(R^A)CO_2R^B$, and (ii) optionally substituted with 1 or 2 substituents each of which is independently:
(1) aryl,
(2) —$C_{1-6}$ alkyl substituted with aryl,
(3) —HetA,
(4) —$C(=O)$—HetA; or
(5) -HetB;
  wherein each HetA is independently a $C_{4-7}$ azacycloalkyl or a $C_{3-6}$ diazacycloalkyl, either of which is optionally substituted with from 1 to 3 substituents each of which is independently oxo or $C_{1-6}$ alkyl; and
  wherein each HetB is a 5- or 6-membered heteroaromatic ring containing from 1 to 4 heteroatoms independently selected from N, O and S, wherein the heteroaromatic ring is optionally substituted with from 1 to 4 substituents each of which is independently halo, —$C_{1-6}$ alkyl, —$C_{1-6}$ haloalkyl, —O—$C_{1-6}$ alkyl, —O—$C_{1-6}$ haloalkyl, or hydroxy; or (B) a 5- or 6-membered heteroaromatic ring containing from 1 to 4 heteroatoms independently selected from N, O and S; wherein the heteroaromatic ring is:
(i) optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or hydroxy, and
(ii) optionally substituted with 1 or 2 substituents each of which is independently aryl or —$C_{1-6}$ alkyl substituted with aryl;

$R^2$, $R^3$, $R^4$ and $R^5$ are defined as follows:
(A) $R^2$, $R^3$, $R^4$ and $R^5$ are each independently:
(1) —H,
(2) —$C_{1-6}$ alkyl, which is optionally substituted with —OH, —O—$C_{1-6}$ alkyl, —O—$C_{1-6}$ haloalkyl, —CN, —$N(R^A)R^B$, —$C(=O)N(R^A)R^B$, —$C(=O)R^A$, —$CO_2R^A$, —$S(O)_nR^A$, —$SO_2N(R^A)R^B$, —$N(R^A)C(=O)R^B$, —$N(R^A)CO_2R^B$, —$N(R^A)SO_2R^B$, —$N(R^A)SO_2N(R^A)R^B$, —$N(R^A)C(=O)N(R^A)R^B$, or —$OC(=O)N(R^A)R^B$,
(3) —$C_{1-6}$ haloalkyl,
(4) CycA,
(5) AryA,
(6) HetC, or
(7) —$C_{1-6}$ alkyl substituted with CycA, AryA, or HetC;
(B) $R^2$ and $R^4$ together with the carbon atoms to which each is attached form a carbon-carbon double bond; and $R^3$ and $R^5$ are each independently as defined in part A above;
(C) $R^2$ and $R^3$ together with the carbon atom to which they are both attached form a 3- to 8-membered saturated carbocyclic ring which is optionally substituted with from 1 to 4 substituents each of which is independently —OH, —$C_{1-6}$ alkyl, —$C_{1-6}$ haloalkyl, —O—$C_{1-6}$ alkyl, or —O—$C_{1-6}$ haloalkyl; and $R^4$ and $R^5$ are each independently as defined in part A above; or
(D) $R^4$ and $R^5$ together with the carbon atom to which they are both attached form a 3- to 8-membered saturated carbocyclic ring which is optionally substituted with from 1 to 4 substituents each of which is independently —OH, —$C_{1-6}$ alkyl, —$C_{1-6}$ haloalkyl, —O—$C_{1-6}$ alkyl, or —O—$C_{1-6}$ haloalkyl; and $R^2$ and $R^3$ are each independently as defined in part A above;

$R^6$ is:
(1) —H,
(2) —$C_{1-6}$ alkyl, which is optionally substituted with —OH, —O—$C_{1-6}$ alkyl, —O—$C_{1-16}$ haloalkyl, —CN, —$N(R^A)R^B$, —$C(=O)N(R^A)R^B$, —$C(=O)R^A$, —$CO_2R^A$, —$S(O)_nR^A$, —$SO_2N(R^A)R^B$, —$N(R^A)C(=O)R^B$, —$N(R^A)CO_2R^B$, —$N(R^A)SO_2R^B$, —$N(R^A)SO_2N(R^A)R^B$, —$N(R^A)C(=O)N(R^A)R^B$, or —$OC(=O)N(R^A)R^B$,
(3) —$C_{1-6}$ haloalkyl,
(4) CycA,
(5) AryA,
(6) HetC, or
(7) —$C_{1-6}$ alkyl substituted with CycA, AryA, or HetC;

$R^7$ and $R^8$ are each independently:
(1) —H,
(2) —$C_{1-6}$ alkyl, which is optionally substituted with —OH, —O—$C_{1-6}$ alkyl, —O—$C_{1-6}$ haloalkyl, —CN, —$N(R^A)R^B$, —$C(=O)N(R^A)R^B$, —$C(=O)R^A$, —$CO_2R^A$, —$S(O)_nR^A$, —$SO_2N(R^A)R^B$, —$N(R^A)C(=O)R^B$, —$N(R^A)CO_2R^B$, —$N(R^A)SO_2R^B$, —$N(R^A)SO_2N(R^A)R^B$, —$N(R^A)C(=O)N(R^A)R^B$, or —$OC(=O)N(R^A)R^B$,
(3) —$C_{1-6}$ haloalkyl,
(4) —$C(=O)R^A$,
(5) —$CO_2R^A$,
(6) —$C(=O)N(R^A)R^B$,
(7) —$N(R^A)SO_2N(R^A)R^B$,
(8) —$R^K$,
(9) —$C(=O)$—$R^K$,
(10) —$C(=O)N(R^A)$—$R^K$,
(11) —$C(=O)N(R^A)$—$C_{1-6}$ alkylene-$R^K$, or
(12) —$C_{1-6}$ alkyl substituted with $R^K$, —$C(=O)$—$R^K$, —$C(=O)N(R^A)$—$R^K$, or —$C(=O)N(R^A)$—$C_{1-6}$ alkylene-$R^K$;

or alternatively $R^7$ and $R^8$ together with the carbon atom to which they are both attached form a 3- to 8-membered saturated carbocyclic ring which is optionally substituted with from 1 to 4 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl;

$R^9$ is:
(1) —H,
(2) —$C_{1-6}$ alkyl, which is optionally substituted with —OH, —O—$C_{1-6}$ alkyl, —O—$C_{1-6}$ haloalkyl, —CN, —$N(R^A)R^B$, —$C(=O)N(R^A)R^B$, —$C(=O)R^A$, —$CO_2R^A$, —$S(O)_nR^A$, —$SO_2N(R^A)R^B$, —$N(R^A)C(=O)R^B$, —$N(R^A)CO_2R^B$, —$N(R^A)SO_2R^B$, —$N(R^A)SO_2N(R^A)R^B$, —$N(R^A)C(=O)N(R^A)R^B$, or —$OC(=O)N(R^A)R^B$,
(3) —$C_{1-6}$ haloalkyl,
(4) CycA,
(5) AryA,
(6) HetC, or (7) —$C_{1-6}$ alkyl substituted with CycA, AryA, or HetC;

each n is independently an integer equal to zero, 1, or 2;

each $R^A$ is independently H or $C_{1-6}$ alkyl;

each $R^B$ is independently H or $C_{1-6}$ alkyl;

each $R^K$ is independently CycA, AryA, or HetC;

each CycA is independently a $C_{3-8}$ cycloalkyl, which is optionally substituted with from 1 to 4 substituents each of which is halogen, —OH, —$C_{1-6}$ alkyl, —$C_{1-6}$ haloalkyl, —O—$C_{1-6}$ alkyl, or —O—$C_{1-6}$ haloalkyl;

each AryA is independently an aryl, which is (a) optionally substituted with from 1 to 5 substituents each of which is independently —$C_{1-6}$ alkyl, —$C_{1-6}$ alkylene-OH, —$C_{1-6}$ alkylene-O—$C_{1-6}$ alkyl, —$C_{1-6}$ alkylene-O—$C_{1-6}$ haloalkyl, —$C_{1-6}$ alkylene-N($R^A$)$R^B$, —$C_{1-6}$ alkylene-C(=O)N($R^A$)$R^B$, —$C_{1-6}$ alkylene-C(=O)$R^A$, —$C_{1-6}$ alkylene-CO$_2$$R^A$, —$C_{1-6}$ alkylene-S(O)$_n$$R^A$, —O—$C_{1-6}$ alkyl, —$C_{1-6}$ haloalkyl, —O—$C_{1-6}$ haloalkyl, —OH, halo, —N($R^A$)$R^B$, —C(=O)N($R^A$)$R^B$, —C(=O)$R^A$, —CO$_2$$R^A$, —S(O)$_n$$R^A$, or —SO$_2$N($R^A$)$R^B$, and (b) optionally substituted with $C_{3-8}$ cycloalkyl, aryl, HetD, or —$C_{1-6}$ alkyl substituted with $C_{3-8}$ cycloalkyl, aryl, or HetD;

each HetC is independently a 4- to 7-membered saturated or unsaturated heterocyclic ring containing at least one carbon atom and from 1 to 4 heteroatoms independently selected from N, O and S, wherein the heterocyclic ring is (a) optionally substituted with from 1 to 4 substituents each of which is halogen, —$C_{1-6}$ alkyl, —$C_{1-6}$ haloalkyl, —O—$C_{1-6}$ alkyl, —O—$C_{1-6}$ haloalkyl, OH, or oxo, and (b) optionally substituted with $C_{3-8}$ cycloalkyl, aryl, HetD, or —$C_{1-6}$ alkyl substituted with $C_{3-8}$ cycloalkyl, aryl, or HetD;

each HetD is independently a 4- to 7-membered saturated or unsaturated heterocyclic ring containing at least one carbon atom and from 1 to 4 heteroatoms independently selected from N, O and S; and each aryl is independently (i) phenyl or (ii) a 9- or 10-membered bicyclic, fused carbocylic ring system in which at least one ring is aromatic.

The present invention also includes pharmaceutical compositions containing a compound of the present invention and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes compounds of Formula I above, and pharmaceutically acceptable salts thereof. These compounds and pharmaceutically acceptable salts thereof are UV integrase inhibitors. More particularly, the compounds of Formula I inhibit the integrase function of HIV-1 integrase.

A first embodiment of the present invention is a compound of Formula I, or a pharmaceutically acceptable salt thereof, wherein Z is N—$R^9$; and all other variables are as originally defined (i.e., as defined in the Summary of the Invention). In other words, in this embodiment, the compound of Formula I is a compound of Formula Ia:

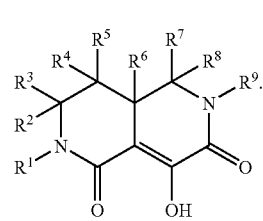

(Ia)

A second embodiment of the present invention is a compound of Formula I, or a pharmaceutically acceptable salt thereof, wherein $R^1$ is CH$_2$—$R^J$; and all other variables are as originally defined (i.e., as defined in the Summary of the Invention), or as defined in the first embodiment.

A third embodiment of the present invention is a compound of Formula I, or a pharmaceutically acceptable salt thereof, wherein $R^1$ is CH$_2$—$R^J$; $R^J$ is phenyl, pyridyl, quinolinyl, isoquinolinyl, cinnolinyl, or quinazolinyl, any of which is (a) optionally substituted with from 1 to 4 substituents each of which is independently:

(1) —$C_{1-4}$ alkyl,
(2) —O—$C_{1-4}$ alkyl,
(3) —$C_{1-4}$ haloalkyl,
(4) —O—$C_{1-4}$ haloalkyl,
(5) halo,
(6) —CN,
(7) —N($R^A$)$R^B$,
(8) —C(=O)N($R^A$)$R^B$,
(9) —S(=O)$R^A$,
(10) —SO$_2$$R^A$,
(11) —N($R^A$)SO$_2$$R^B$,
(12) —N($R^A$)SO$_2$N($R^A$)$R^B$,
(13) —N($R^A$)C(=O)$R^B$, or
(14) —N($R^A$)C(=O)—C(=O)N($R^A$)$R^B$, and (b) optionally substituted with phenyl, benzyl, -HetA, or —C(=O)—HetA; wherein each HetA is independently a $C_{4-7}$ azacycloalkyl or a $C_{3-6}$ diazacycloalkyl, either of which is optionally substituted with from 1 to 3 substituents each of which is independently oxo or $C_{1-4}$ alkyl; and with the proviso that when HetA is attached to the rest of the compound via the —C(=O)— moiety, the HetA is attached to the —C(=O)— via a ring N atom;

and all other variables are as originally defined, or as defined in the first embodiment.

A fourth embodiment of the present invention is a compound of Formula I, or a pharmaceutically acceptable salt thereof, wherein $R^1$ is CH$_2$—$R^J$; $R^J$ is phenyl optionally substituted with from 1 to 3 substituents each of which is independently: (1) —$C_{1-4}$ alkyl, (2) —$C_{1-4}$ fluoroalkyl, (3) —O—$C_{1-14}$ alkyl, (4) —O—$C_{1-4}$ fluoroalkyl, (5) halo, (6) —CN, (7) —C(=O)N($R^A$)$R^B$, or (8) —SO$_2$$R^A$; and all other variables are as originally defined, or as defined in the first embodiment.

A fifth embodiment of the present invention is a compound of Formula I, or a pharmaceutically acceptable salt thereof, wherein $R^1$ is CH$_2$—$R^J$; $R^J$ is 4-fluorophenyl; and all other variables are as originally defined, or as defined in the first embodiment.

A sixth embodiment of the present invention is a compound of Formula I, or a pharmaceutically acceptable salt thereof, wherein $R^2$, $R^3$, $R^4$ and $R^5$ are defined as follows:

(A) $R^2$ and $R^4$ are as originally defined in part A of the above definition of $R^2$, $R^3$, $R^4$ and $R^5$; and $R^3$ and $R^5$ are both H;

(B) $R^2$ and $R^4$ are as originally defined in part B of the above definition of $R^2$, $R^3$, $R^4$ and $R^5$; and $R^3$ and $R^5$ are both H;

(C) $R^2$ and $R^3$ are as originally defined in part C of the above definition of $R^2$, $R^3$, $R^4$ and $R^5$; and $R^4$ and $R^5$ are both H; or (D) $R^4$ and $R^5$ are as originally defined in part D of the above definition of $R^2$, $R^3$, $R^4$ and $R^5$; and $R^2$ and $R^3$ are both H;

and all other variables are as originally defined or as defined in any one of the preceding embodiments.

A seventh embodiment of the present invention is a compound of Formula I, or a pharmaceutically acceptable salt thereof, wherein $R^2$, $R^3$, $R^4$ and $R^5$ are defined as follows:

(A) $R^3$ and $R^5$ are both H; and $R^2$ and $R^4$ are each independently (1) —H, (2) —$C_{1-4}$ alkyl, (3) —$C_{1-4}$ fluoroalkyl, (4) $C_{3-6}$ cycloalkyl, (5) phenyl, or (6) benzyl;

(B) $R^2$ and $R^4$ together with the carbon atoms to which each is attached form a carbon-carbon double bond; and $R^3$ and $R^5$ are both H;

(C) $R^2$ and $R^3$ together with the carbon atom to which they are both attached form a 3- to 7-membered saturated carbocyclic ring; and $R^4$ and $R^5$ are both H; or (D) $R^4$ and $R^5$ together with the carbon atom to which they are both attached form a 3- to 7-membered saturated carbocyclic ring; and $R^2$ and $R^3$ are both H;

and all other variables are as originally defined or as defined in any one of the preceding embodiments.

An eighth embodiment of the present invention is a compound of Formula I, or a pharmaceutically acceptable salt thereof, wherein $R^2$, $R^3$, $R^4$ and $R^5$ are all H; and all other variables are as originally defined or as defined in any one of the preceding embodiments.

A ninth embodiment of the present invention is a compound of Formula I, or a pharmaceutically acceptable salt thereof, wherein $R^6$ is: (1) —H, (2) —$C_{1-6}$ alkyl, (3) —$C_{1-6}$ fluoroalkyl, (4) CycA, (5) AryA, or (6) —$C_{1-6}$ alkyl substituted with AryA; and all other variables are as originally defined or as defined in any one of the preceding embodiments.

A tenth embodiment of the present invention is a compound of Formula I, or a pharmaceutically acceptable salt thereof, wherein $R^6$ is H, —$C_{1-4}$ alkyl, $CF_3$, cyclopropyl, phenyl or benzyl; and all other variables are as originally defined or as defined in any one of the preceding embodiments.

An eleventh embodiment of the present invention is a compound of Formula I, or a pharmaceutically acceptable salt thereof, wherein $R^6$ is H; and all other variables are as originally defined or as defined in any one of the preceding embodiments.

A twelfth embodiment of the present invention is a compound of Formula I, or a pharmaceutically acceptable salt thereof, wherein $R^7$ and $R^8$ are each independently: (1) —H, (2) —$C_{1-6}$ alkyl, (3) —$CO_2R^A$, (4) —C(=O)N($R^A$)$R^B$, (5) —$R^K$, (6) —C(=O)—$R^K$, (7) —C(=O)N($R^A$)—$R^K$, or (8) —C(=O)N($R^A$)—$C_{1-6}$ alkylene-$R^K$; or alternatively $R^7$ and $R^8$ together with the carbon atom to which they are both attached form a 3- to 7-membered saturated carbocyclic ring; and all other variables are as originally defined or as defined in any one of the preceding embodiments.

A thirteenth embodiment of the present invention is a compound of Formula I, or a pharmaceutically acceptable salt thereof, wherein $R^7$ is H or —$C_{1-4}$ alkyl; and $R^8$ is: (1) —H, (2) —$C_{1-4}$ alkyl, (3) —$CO_2$—$C_{1-4}$ alkyl, (4) —C(=O)NH($C_{1-4}$ alkyl), (5) —C(=O)N($C_{1-4}$ alkyl)$_2$, (6) CycA, (7) HetF, (8) —C(=O)—HetE, wherein HetE is a 4- to 7-membered saturated heterocyclic ring containing at least one carbon atom and from 1 to 4 heteroatoms selected from 1 to 4 N atoms, zero or 1 oxygen atom, and zero or 1 sulfur atom, wherein the saturated heterocyclic is optionally substituted with from 1 to 3 substituents each of which is independently oxo or $C_{1-4}$ alkyl; and with the proviso that the saturated heterocyclic is attached to the —C(=O)— via a ring N atom, or (9) —C(=O)N($R^A$)—$(CH_2)_{1-2}$-HetF, wherein HetF is a 5- or 6-membered heteroaromatic ring containing from 1 to 4 heteroatoms independently selected from N, O and S, wherein the heteroaromatic ring is optionally substituted with 1 or 2 substituents each of which is independently a $C_{1-4}$ alkyl;

or alternatively $R^7$ and $R^8$ together with the carbon atom to which they are both attached form a 3- to 6-membered saturated carbocyclic ring; and all other variables are as originally defined or as defined in any one of the preceding embodiments.

A fourteenth embodiment of the present invention is a compound of Formula I, or a pharmaceutically acceptable salt thereof, wherein $R^7$ is H or —$C_{1-4}$ alkyl; and $R^8$ is: (1) —H, (2) —$C_{1-4}$ alkyl, (3) —$CO_2$—$C_{1-4}$ alkyl, (4) —C(=O)NH ($C_{1-4}$ alkyl), (5) —C(=O)N($C_{1-4}$ alkyl)$_2$, (6) CycA, (7) —C(=O)—HetE, wherein HetE is a 4- to 7-membered saturated heterocyclic ring containing at least one carbon atom and from 1 to 4 heteroatoms selected from 1 to 4 N atoms, zero or 1 oxygen atom, and zero or 1 sulfur atom, wherein the saturated heterocyclic is optionally substituted with from 1 to 3 substituents each of which is independently oxo or $C_{1-4}$ alkyl; and with the proviso that the saturated heterocyclic is attached to the —C(=O)— via a ring N atom, or (8) —C(=O)N($R^A$)—$(CH_2)_{1-2}$-HetF, wherein HetF is a 5- or 6-membered heteroaromatic ring containing from 1 to 4 heteroatoms independently selected from N, O and S, wherein the heteroaromatic ring is optionally substituted with 1 or 2 substituents each of which is independently a $C_{1-4}$ alkyl;

or alternatively $R^7$ and $R^8$ together with the carbon atom to which they are both attached form a 3- to 6-membered saturated carbocyclic ring; and all other variables are as originally defined or as defined in any one of the preceding embodiments.

A fifteenth embodiment of the present invention is a compound of Formula I, or a pharmaceutically acceptable salt thereof, wherein $R^9$ is: (1) —H, (2) —$C_{1-6}$ alkyl (3) —$C_{1-6}$ fluoroalkyl, (4) CycA, or (5) —$C_{1-6}$ alkyl substituted with CycA, AryA, or HetC; and all other variables are as originally defined or as defined in any one of the preceding embodiments.

A sixteenth embodiment of the present invention is a compound of Formula I, or a pharmaceutically acceptable salt thereof, wherein $R^9$ is: (1) —H, (2)-$C_{1-4}$ alkyl, (3) —$CH_2CF_3$, (4) —$C_{3-6}$ cycloalkyl, (5) —$CH_2$—$C_{3-6}$ cycloalkyl, or (6) —$CH_2$-phenyl; and all other variables are as originally defined or as defined in any one of the preceding embodiments.

A seventeenth embodiment of the present invention is a compound of Formula I, or a pharmaceutically acceptable salt thereof, wherein $R^9$ is H, methyl, ethyl, n-propyl, isopropyl, —$CH_2CF_3$, cyclopropyl, or —$CH_2$-cyclopropyl.

An eighteenth embodiment of the present invention is a compound of Formula I, or a pharmaceutically acceptable salt thereof, wherein each CycA is independently a $C_{3-7}$ cycloalkyl, which is optionally substituted with from 1 to 4 substituents each of which is halogen, —OH, —$C_{1-6}$ alkyl, —$C_{1-6}$ haloalkyl, —O—$C_{1-6}$ alkyl, or —O—$C_{1-16}$ haloalkyl; and all other variables are as originally defined or as defined in any one of the preceding embodiments.

A nineteenth embodiment of the present invention is a compound of Formula I, or a pharmaceutically acceptable salt thereof, wherein each AryA is independently an aryl, which is (a) optionally substituted with from 1 to 5 substituents each of which is independently —$C_{1-6}$ alkyl, —$C_{1-6}$ alkylene-OH, —$C_{1-6}$ alkylene-O—$C_{1-6}$ alkyl, —$C_{1-6}$ alkylene-O—$C_{1-6}$ haloalkyl, —$C_{1-6}$ alkylene-N($R^A$)$R^B$, —$C_{1-6}$ alkylene-C(=O)N($R^A$)$R^B$, —$C_{1-6}$ alkylene-C(=O)$R^A$, —$C_{1-6}$ alkylene-CO$_2R^A$, —$C_{1-6}$ alkylene-S(O)$_nR^A$, —O—$C_{1-6}$ alkyl, —$C_{1-6}$ haloalkyl, —O—$C_{1-16}$ haloalkyl, —OH, halo, —N($R^A$)$R^B$, —C(=O)N($R^A$)$R^B$, —C(=O)$R^A$, —CO$_2R^A$, —S(O)$_nR^A$, or —SO$_2$N($R^A$)$R^B$, and (b) optionally substituted with $C_{3-6}$ cycloalkyl, phenyl, HetD, —CH$_2$—$C_{3-6}$ cycloalkyl, benzyl, or —CH$_2$-HetD;

and all other variables are as originally defined or as defined in any one of the preceding embodiments.

A twentieth embodiment of the present invention is a compound of Formula I, or a pharmaceutically acceptable salt thereof, wherein each HetC is independently:

(i) a 4- to 7-membered saturated heterocyclic ring containing at least one carbon atom and from 1 to 4 heteroatoms independently selected from N, O and S, wherein the saturated ring is:
  (a) optionally substituted with from 1 to 4 substituents each of which is halogen, —$C_{1-6}$ alkyl, —$C_{1-6}$ haloalkyl, —O—$C_{1-16}$ alkyl, —O—$C_{1-6}$ haloalkyl, OH, or oxo, and
  (b) optionally substituted with $C_{3-6}$ cycloalkyl, phenyl, HetD, —CH$_2$—$C_{3-6}$ cycloalkyl, benzyl, or —CH$_2$-HetD;

(ii) a 5- or 6-membered heteroaromatic ring containing from 1 to 4 heteroatoms independently selected from N, O and S, wherein the heteroaromatic ring is:
  (a) optionally substituted with from 1 to 4 substituents each of which is halogen, —$C_{1-6}$ alkyl, —$C_{1-6}$ haloalkyl, —O—$C_{1-6}$ alkyl, —O—$C_{1-6}$ haloalkyl, or OH, and
  (b) optionally substituted with $C_{3-6}$ cycloalkyl, phenyl, HetD, —CH$_2$—$C_{3-6}$ cycloalkyl, benzyl, or —CH$_2$-HetD;

and all other variables are as originally defined or as defined in any one of the preceding embodiments.

A twenty-first embodiment of the present invention is a compound of Formula I, or a pharmaceutically acceptable salt thereof, wherein each HetD is independently (i) a 4- to 7-membered saturated heterocyclic ring containing at least one carbon atom and from 1 to 4 heteroatoms independently selected from N, O and S or (ii) a 5- or 6-membered heteroaromatic ring containing from 1 to 4 heteroatoms independently selected from N, O and S; and all other variables are as originally defined or as defined in any one of the preceding embodiments.

A twenty-second embodiment of the present invention is a compound of Formula I, or a pharmaceutically acceptable salt thereof, wherein each aryl is independently phenyl, indenyl, indanyl, naphthyl, or tetrahydronaphthyl; and all other variables are as originally defined or as defined in any one of the preceding embodiments. In an aspect of this embodiment, each aryl is independently phenyl or naphthyl. In another aspect each aryl is phenyl.

A twenty-third embodiment of the present invention is a compound of Formula I, or a pharmaceutically acceptable salt thereof, wherein each $R^A$ and $R^B$ is independently H or $C_{1-4}$ alkyl; and all other variables are as originally defined or as defined in any one of the preceding embodiments.

A twenty-fourth embodiment of the present invention is a compound of Formula I, or a pharmaceutically acceptable salt thereof, wherein each $R^A$ and $R^B$ is independently H, methyl, or ethyl; and all other variables are as originally defined or as defined in any one of the preceding embodiments. In an aspect of this embodiment, each $R^A$ and $R^B$ is independently H or methyl.

A first class of the present invention includes compounds of Formula II, and pharmaceutically acceptable salts thereof:

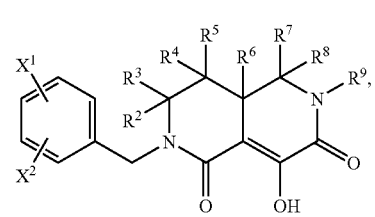

(II)

wherein:

$X^1$ and $X^2$ are each independently —H, —$C_{1-4}$ alkyl, —O—$C_{1-4}$ alkyl, —$C_{1-4}$ haloalkyl, —O—$C_{1-4}$ haloalkyl, halo, —CN, —N($R^A$)$R^B$, —C(=O)N($R^A$)$R^B$, or —S(O)$_n$$R^A$, wherein n is an integer equal to zero, 1, or 2;

$R^2$, $R^3$, $R^4$ and $R^5$ are defined as follows:
  (A) $R^2$ and $R^4$ are each independently —H, —$C_{1-4}$ alkyl, —$C_{1-4}$ fluoroalkyl, $C_{3-6}$ cycloalkyl, phenyl, or benzyl; and $R^4$ and $R^5$ are both H;
  (B) $R^2$ and $R^4$ together with the carbon atoms to which each is attached form a carbon-carbon double bond; and $R^3$ and $R^5$ are both H;
  (C) $R^2$ and $R^3$ together with the carbon atom to which they are both attached form cyclopropyl; and $R^4$ and $R^5$ are both H; or
  (D) $R^4$ and $R^5$ together with the carbon atom to which they are both attached form cyclopropyl; and $R^2$ and $R^3$ are both H;

$R^6$ is H, —$C_{1-4}$ alkyl, CF$_3$, cyclopropyl, phenyl or benzyl;

$R^7$ is H or —$C_{1-4}$ alkyl;

$R^8$ is —H, —$C_{1-4}$ alkyl, —CO$_2$—$C_{1-4}$ alkyl, —C(=O)NH($C_{1-4}$ alkyl), —C(=O)N($C_{1-4}$ alkyl)$_2$, $C_{3-6}$ cycloalkyl, HetF, —C(=O)—HetE, or —C(=O)N($R^A$)—(CH$_2$)$_{1-2}$-HetF; wherein HetE is a 4- to 7-membered saturated heterocyclic ring containing at least one carbon atom and from 1 to 4 heteroatoms selected from 1 to 4 N atoms, zero or 1 oxygen atom, and zero or 1 sulfur atom, wherein the saturated heterocyclic is optionally substituted with from 1 to 3 substituents each of which is independently oxo or $C_{1-4}$ alkyl; and with the proviso that the saturated heterocyclic is attached to the —C(=O)— via a ring N atom; and HetF is a 5- or 6-membered heteroaromatic ring containing from 1 to 4 heteroatoms independently selected from N, O and S, wherein the heteroaromatic ring is optionally substituted with 1 or 2 substituents each of which is independently a $C_{1-4}$ alkyl;

or alternatively $R^7$ and $R^8$ together with the carbon atom to which they are both attached form a 3- to 6-membered saturated carbocyclic ring;

$R^9$ is —H, —$C_{1-4}$ alkyl, —$CH_2CF_3$, —$C_{3-6}$ cycloalkyl, —$CH_2$—$C_{3-6}$ cycloalkyl, or —$CH_2$-phenyl;

each $R^A$ is independently H or $C_{1-4}$ alkyl; and each $R^B$ is independently H or $C_{1-4}$ alkyl.

A first sub-class of the first class includes compounds of Formula II, and pharmaceutically acceptable salts thereof, wherein $R^8$ is —H, —$C_{1-4}$ alkyl, —$CO_2$—$C_{1-4}$ alkyl, —C(=O)NH($C_{1-4}$ alkyl), —C(=O)N($C_{1-4}$ alkyl)$_2$, $C_{3-6}$ cycloalkyl, —C(=O)—HetE, or —C(=O)N($R^A$)—(CH$_2$)$_{1-2}$-HetF; and all other variables are as originally defined in the first class.

A second sub-class of the first class includes compounds of Formula II, and pharmaceutically acceptable salts thereof, wherein:

$X^1$ and $X^2$ are each independently H, fluoro, chloro, methyl, trifluoromethyl, methoxy, CN, —$SO_2CH_3$, —C(=O)NH(CH$_3$), or —C(=O)N(CH$_3$)$_2$;

$R^2$, $R^3$, $R^4$ and $R^5$ are all H;

$R^6$ is H, methyl, cyclopropyl, or phenyl;

$R^7$ is H or methyl;

$R^8$ is —H, —$C_{1-4}$ alkyl, —$CO_2$—$C_{1-4}$ alkyl, —C(=O)NH($C_{1-4}$ alkyl), —C(=O)N($C_{1-4}$ alkyl)$_2$, $C_{3-6}$ cycloalkyl, HetF, —C(=O)—HetE, or —C(=O)N($R^A$)—(CH$_2$)$_{1-2}$-HetF; wherein HetE is selected from the group consisting of:

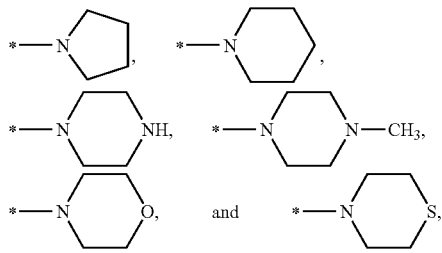

wherein the asterisk *denotes the point of attachment to the —C(=O) moiety; and

HetF is selected from the group consisting of pyrrolyl, imidazolyl, triazolyl, tetrazolyl, oxazolyl, isooxazolyl, pyridyl, pyrimidinyl, and pyrazinyl;

or alternatively $R^7$ and $R^8$ together with the carbon atom to which they are both attached form cyclopropyl, cyclobutyl, cyclopentyl, or cyclohexyl; and $R^9$ is H, methyl, ethyl, n-propyl, isopropyl, —$CH_2CF_3$, cyclopropyl, or —$CH_2$-cyclopropyl.

A third sub-class of the first class includes compounds of Formula II, and pharmaceutically acceptable salts thereof, wherein $R^8$ is —H, —$C_{1-4}$ alkyl, —$CO_2$—$C_{1-4}$ alkyl, —C(=O)NH($C_{1-4}$ alkyl), —C(=O)N($C_{1-4}$ alkyl)$_2$, $C_{3-6}$ cycloalkyl, —C(=O)—HetE, or —C(=O)N($R^A$)—(CH$_2$)$_{1-2}$- HetF; and all other variables are as defined in the second sub-class.

Another embodiment of the present invention is a compound, or a pharmaceutically acceptable salt thereof, selected from the group consisting of the compounds set forth in Examples 1 to 18 below.

Other embodiments of the present invention include the following:

(a) A pharmaceutical composition comprising an effective amount of a compound of Formula I and a pharmaceutically acceptable carrier.

(b) A pharmaceutical composition which comprises the product prepared by combining (e.g., mixing) an effective amount of a compound of Formula I and a pharmaceutically acceptable carrier.

(c) The pharmaceutical composition of (a) or (b), further comprising an effective amount of an HIV infection/AIDS treatment agent selected from the group consisting of HIV/AIDS antiviral agents, immunomodulators, and anti-infective agents.

(d) The pharmaceutical composition of (c), wherein the HIV infection/AIDS treatment agent is an antiviral selected from the group consisting of HIV protease inhibitors, non-nucleoside HIV reverse transcriptase inhibitors, and nucleoside HIV reverse transcriptase inhibitors.

(e) A pharmaceutical combination which is (i) a compound of Formula I and (ii) an HIV infection/AIDS treatment agent selected from the group consisting of HIV/AIDS antiviral agents, immunomodulators, and anti-infective agents; wherein the compound of Formula I and the HIV infection/AIDS treatment agent are each employed in an amount that renders the combination effective for inhibiting HIV integrase, for treating or preventing infection by HIV, or for preventing, treating or delaying the onset of AIDS.

(f) The combination of (e), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject an effective amount of a compound of Formula I.

(h) A method of preventing or treating infection by HIV in a subject in need thereof which comprises administering to the subject an effective amount of a compound of Formula I.

(i) The method of (h), wherein the compound of Formula (I) is administered in combination with an effective amount of at least one antiviral selected from the group consisting of HIV protease inhibitors, non-nucleoside HIV reverse transcriptase inhibitors, and nucleoside HIV reverse transcriptase inhibitors.

(j) A method of preventing, treating or delaying the onset of AIDS in a subject in need thereof which comprises administering to the subject an effective amount of a compound of Formula I.

(k) The method of (j), wherein the compound is administered in combination with an effective amount of at least one antiviral selected from the group consisting of HIV protease inhibitors, non-nucleoside HIV reverse transcriptase inhibitors, and nucleoside HIV reverse transcriptase inhibitors (l) A method of inhibiting HIV integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV integrase, (b) preventing or treating infection by HIV, or (c) preventing, treating or delaying the onset of AIDS. In these uses, the compounds of the present invention can optionally be employed in combination with one or more HIV/AIDS treatment agents selected from HIV AIDS antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "alkylene" refers to any linear or branched chain alkylene group (or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The term "cycloalkyl" refers to any cyclic ring of an alkane having a number of carbon atoms in the specified range. Thus, for example, "$C_{3-8}$ cycloalkyl" (Or "$C_3$-$C_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "$C_{4-7}$ azacycloalkyl" (or "$C_4$-$C_7$ azacycloalkyl") means a saturated cyclic ring consisting of one nitrogen and from four to seven carbon atoms (i.e., pyrrolidinyl, piperidinyl, azepanyl, or octahydroazocinyl).

The term "$C_{3-6}$ diazacycloalkyl" (or "$C_3$-$C_6$ diazacycloalkyl") means a saturated cyclic ring consisting of two nitrogens and from three to six carbon atoms (e.g., imidazolidinyl, pyrazolidinyl, or piperazinyl).

Unless expressly stated to the contrary, all ranges cited herein are inclusive. For example, a heterocyclic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

When any variable (e.g., $R^A$ and $R^B$) occurs more than one time in any constituent or in Formula I, Formula Ia, Formula II, or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "is optionally substituted with from 1 to 5 substituents . . . ") includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., cycloalkyl, aryl, a heteroaromatic ring, or a saturated heterocyclic ring) provided such ring substitution is chemically allowed and results in a stable compound.

Unless expressly stated to the contrary, an "unsaturated" ring is a partially or fully unsaturated ring.

In instances where a hydroxy (—OH) substituent(s) is(are) permitted on a heteroaromatic ring and keto-enol tautomerism is possible, it is understood that the substituent might in fact be present, in whole or in part, in the keto form, as exemplified here for a hydroxypyridinyl substituent:

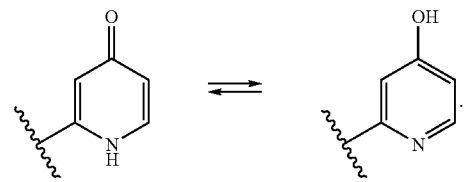

Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and compounds in which the keto and enol forms are both present. Similarly, where a hydroxy substituent is permitted on an unsaturated, non-aromatic heterocyclic ring and keto-enol tautomerism is possible, or an oxo substituent is permitted on a saturated heterocyclic ring and keto-enol tautomerism is possible, it is understood that the substituent might in fact be present as the keto tautomer, the enol tautomer or a mixture thereof. It is understood that compounds of the invention described (e.g., in Formula I) in terms of either the keto form or the enol form include compounds in which either or both the keto and enol forms are present.

Unless expressly stated to the contrary in a particular context, any of the various carbocyclic and heterocyclic rings and ring systems defined herein may be attached to the rest of the compound at any ring atom (i.e., any carbon atom or any heteroatom) provided that a stable compound results. A class of cycloalkyl groups suitable for use in the compounds of the invention (e.g., in the definition of CycA) consists of the $C_{3-6}$ cycloalkyl groups—cyclopropyl, cyclobutyl, cyclopentyl, and cyclohexyl. A class of aryl groups suitable for use in the invention (e.g., independently in the definitions of either or both $R^J$ and AryA) consists of phenyl, indenyl, indanyl, naphthyl, and tetrahydronaphthyl. A sub-class of aryl groups particularly suitable for use in the present invention consists of phenyl and naphthyl. Another aryl sub-class of particular interest is phenyl. A class of 4- to 7-membered saturated heterocyclic rings suitable for use in the present invention (e.g., independently in the definitions of one or more of HetC, HetD and HetE) consists of piperidinyl, morpholinyl, thiomorpholinyl, thiazolidinyl, isothiazolidinyl, oxazolidinyl, isoxazolidinyl, pyrrolidinyl, azetidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl, and dioxanyl. A class of 4- to 7-membered unsaturated heterocyclic rings suitable for use in the present invention (e.g., independently in the definitions of either or both HetC and HetD) consists of the mono-unsaturated counterparts (i.e., containing a single double bond) of the class of saturated heterocyclic rings set forth in the preceding sentence. A class of 5- or 6-membered heteroaromatic rings suitable for use in the present invention (e.g., independently in any one or more of the definitions of $R^J$, HetB, HetC, HetD and HetF) consists of pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl.

Unless expressly stated to the contrary in a particular context, the term "unsaturated heterocyclic ring" refers to rings with partial or complete unsaturation, including non-aromatic rings with one, two or more double bonds and aromatic rings.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As would be recognized by one of ordinary skill in the art, the compounds of the present invention can exist as tautomers such as the following:

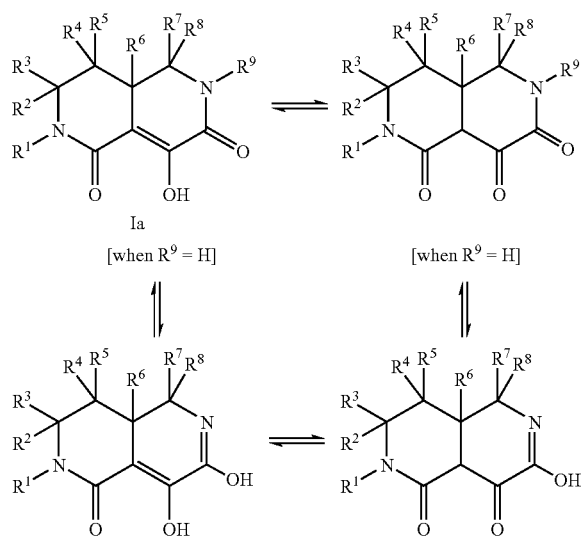

For the purposes of the present invention a reference herein to a compound of Formula I, Formula Ia, or Formula II is a reference to compound I, compound Ia, or compound II per se, or to any one of its tautomers per se, or to mixtures thereof.

The compounds of the present invention have at least one asymmetric center at the fused ring carbon in the naphthyridine ring marked by the arrow in Formula I and Ia:

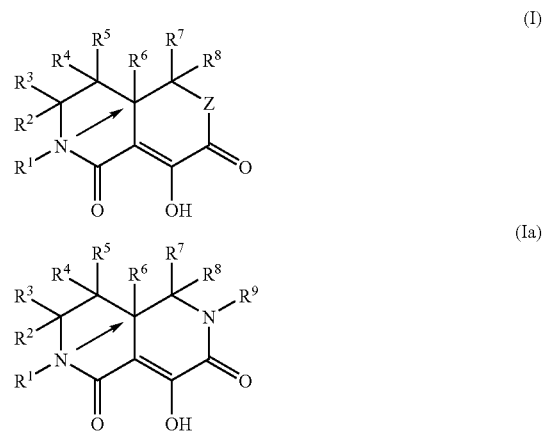

Additional asymmetric centers may be present depending upon the nature of other substituents in the molecule. Each such asymmetric center will independently produce two optical isomers. All possible optical isomers and diastereomers of these compounds, individually and in mixtures, are within the scope of the present invention.

The compounds of the present inventions are useful in the inhibition of HIV integrase, the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HIV infection or AIDS), "administration" and its variants are each understood to include concurrent and sequential provision of the compound or prodrug and other agents.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV integrase and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HIV integrase, preventing or treating HIV infection or preventing, treating or delaying the onset of AIDS, the compounds of the present invention, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, $18^{th}$ edition, edited by A. R. Gennaro, Mack Publishing Co., 1990.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of the HIV integrase inhibitor compounds of the present invention with one or more agents useful in the treatment of HIV infection or AIDS. For example, the compounds of this invention may be effectively administered, whether at periods of pre-exposure and/or post-exposure, in combination with effective amounts of one or more HIV/AIDS antivirals, immunomodulators, antiinfectives, or vaccines useful for treating HIV infection or AIDS, such as those disclosed in Table 1 of WO 01/38332 or in the Table in WO 02/30930. Suitable HIV/AIDS antivirals for use in combination with the compounds of the present invention include, for example, HIV protease inhibitors (e.g., indinavir, atazanavir, lopinavir optionally with ritonavir, saquinavir, or nelfinavir), nucleoside HIV reverse transcriptase inhibitors (e.g., abacavir, lamivudine (3TC), zidovudine (AZT), or tenofovir), and non-nucleoside HIV reverse transcriptase inhibitors (e.g., efavirenz or nevirapine). It will be understood that the scope of combinations of the compounds of this invention with HIV/AIDS antivirals, immunomodulators, anti-infectives or vaccines is not limited to the foregoing substances or to the list in the above-referenced Tables in WO 01/38332 and WO 02/30930, but includes in principle any combination with any pharmaceutical composition useful for the treatment of AIDS. The HIV/AIDS antivirals and other agents will typically be employed in these combinations in their conventional dosage ranges and regimens as reported in the art, including, for example, the dosages described in the *Physicians' Desk Reference*, $57^{th}$ edition, Thomson PDR, 2003. The dosage ranges for a compound of the invention in these combinations are the same as those set forth above.

Abbreviations used in the instant specification, particularly the in the Schemes and Examples, include the following: AIDS=acquired immunodeficiency syndrome; ARC=AIDS related complex; DBU=1,8-diazabicyclo[5.4.0]undec-7-ene; DIEA=diisopropylethylamine (or Hunig's base); DMF=N,N-dimethylformamide; DMSO=dimethylsulfoxide; EDC=1-ethyl-3-(3-dimethylaminopropyl) carbodiimide; ES MS=electrospray mass spectroscopy; Et=ethyl; EtOAc=ethyl acetate; EtOH=ethanol; HIV=human immunodeficiency virus; HOBT or HOBt=1-hydroxy benzotriazole hydrate; HPLC=high performance liquid chromatography; i-Pr=isopropyl; LDA=lithium diisopropylamide; LiHMDS=lithium hexamethyldisilazide; Me=methyl; MeOH=methanol; NMR=nuclear magnetic resonance; Ph=phenyl; t-Bu=tert-butyl; TFA=trifluoroacetic acid; THF=tetrahydrofuran.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Schemes 1 to 3 present methods for preparing compounds of the present invention which contain the 2,3,4,4a,5,6-hexahydro-2,6-naphthyridine-1,7-dione bicyclic nucleus. In Scheme 1, 2-piperidinone 1 is N-alkylated with a halide compound or equivalent reagent in the presence of a base such as sodium hydride to give derivative 2 which contains the $R^1$ variable. Sulfinylation of 2 using methyl phenylsulfinate in the presence of a strong base such as lithium hexamethyldisilazide, followed by heating the sulfinate product in the presence of a base such as sodium carbonate gives unsaturated lactam 3. Michael addition of a nitro compound to 3 in the presence of a base such as 1,8-diazabicyclo[5.4.0]undec-7-ene gives the 4-substituted piperidinone 4, the nitro group in which is reduced to amine 5 using a reagent such as Raney nickel in the presence of hydrogen gas. There are then several pathways to convert 5 to the desired 2,3,4,4a,5,6-hexahydro-2,6-naphthyridine-1,7-dione products. One method involves acylation of 5 with methyl oxalyl chloride or an equivalent reagent to give 6. Oxalamide 6 is then cyclized to 2,3,4,4a,5,6-hexahydro-2,6-naphthyridine-1,7-dione 7 in the presence of a strong base such as lithium hexamethyldisilazide. Introducing the $R^9$ variable on the nitrogen at position 6 in compound 7 is accomplished in an alkylation reaction using a halide compound or an equivalent reagent and a base such as cesium carbonate. During this reaction, in addition to the desired alkylation of the nitrogen at position 6, the hydroxyl group at position 8 may also become alkylated. Removal of the alkyl group on oxygen is achieved in a second step using a reagent such as hydrogen bromide to give compound 10. In a second method, oxalamide 6 is converted to 2,3,4,4a,5,6-hexahydro-2,6-naphthyridine-1,7-dione 10 in a one-pot procedure which involves treatment of 6 with a strong base such as lithium hexamethyldisilazide and a halide compound or equivalent reagent to install the $R^9$ variable, followed by the addition of more strong base such as lithium hexamethyldisilazide to close the ring and furnish 10. In a third method, the amino group in 5 is alkylated with a halide compound or an equivalent reagent to introduce the $R^9$ variable, giving 8. Amine 8 is treated with two or more equivalents of a strong base such as lithium diisopropylamide, and the resulting anion is treated with diethyl oxalate or equivalent reagent to provide 2,3,4,4a,5,6-hexahydro-2,6-naphthyridine-1,7-dione 10. In a fourth method, compound 8 is acylated with methyl oxalyl chloride or equivalent reagent to give 9. Oxalamide 9 is then cyclized to 2,3,4,4a,5,6-hexahydro-2,6-naphthyridine-1,7-dione 10 in the presence of a strong base such as lithium hexamethyldisilazide.

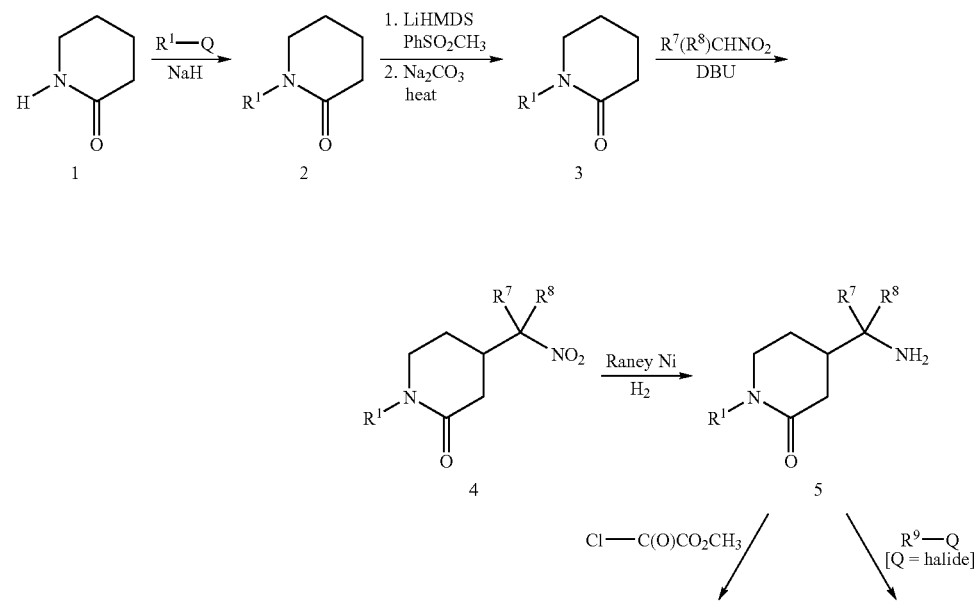

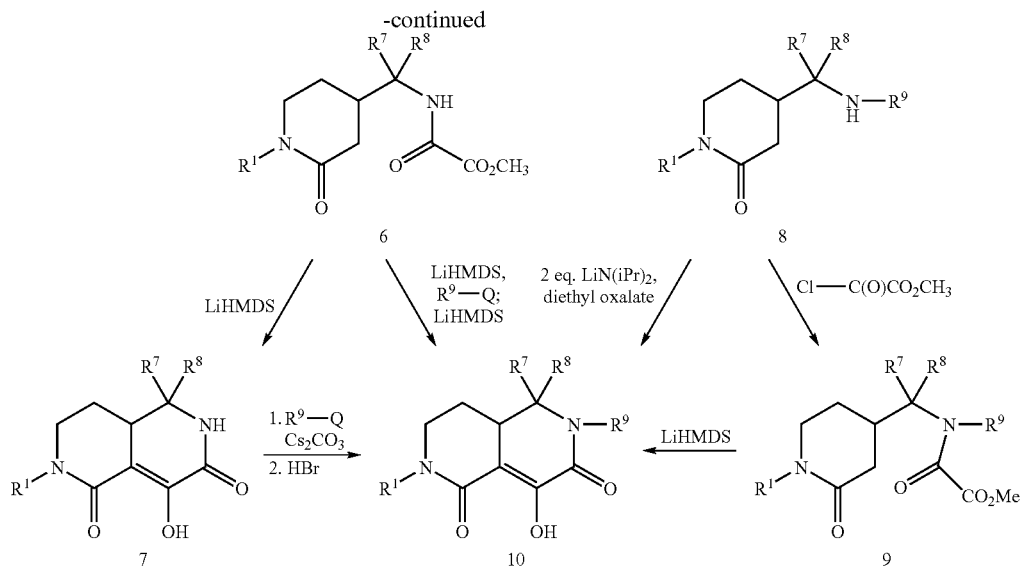

In Scheme 2, nitrile 11 is alkylated with allyl bromide or an equivalent reagent in the presence of a strong base such as lithium diisopropylamide. The product from this reaction is then alkylated with methyl bromoacetate or an equivalent reagent in the presence of a strong base such as lithium diisopropylamide to give olefin ester 12. The ester group in 12 is then converted to an amide by first hydrolyzing the ester to an acid with a base such as sodium hydroxide in water, then the acid is coupled to an amino compound containing the $R^1$ variable using a reagent such as EDC to give olefin amide 13. The olefin in 13 is then oxidatively cleaved using a reagent such as ozone to give an aldehyde which cyclizes onto the amide nitrogen with dehydration under acid catalysis to give dihydropyridinone 14. The double bond in 14 is reduced with a reagent such as hydrogen in the presence of palladium on carbon to give 15. The nitrile in 15 is converted to thioamide 16 using hydrogen sulfide in the presence of a base such as pyridine. Thioamide 16 is then reduced to amine 17 using a reagent such as Raney nickel activated with sodium hydroxide. Amine 17 is treated with methyl oxalyl chloride or an equivalent reagent to give 18. Oxalamide 18 is then treated with a strong base such as lithium hexamethyldisilazide and a halide compound or an equivalent reagent to install the $R^9$ variable, followed by the addition of more strong base such as lithium hexamethyldisilazide to close the ring and furnish 2,3,4,4a,5,6-hexahydro-2,6-naphthyridine-1,7-dione 19.

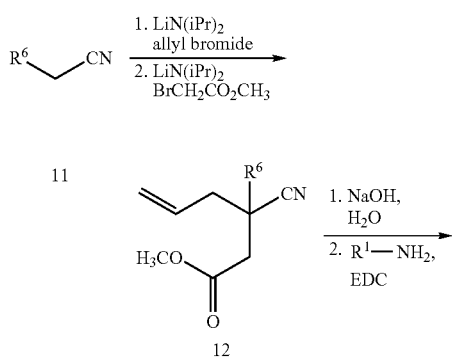

Scheme 2

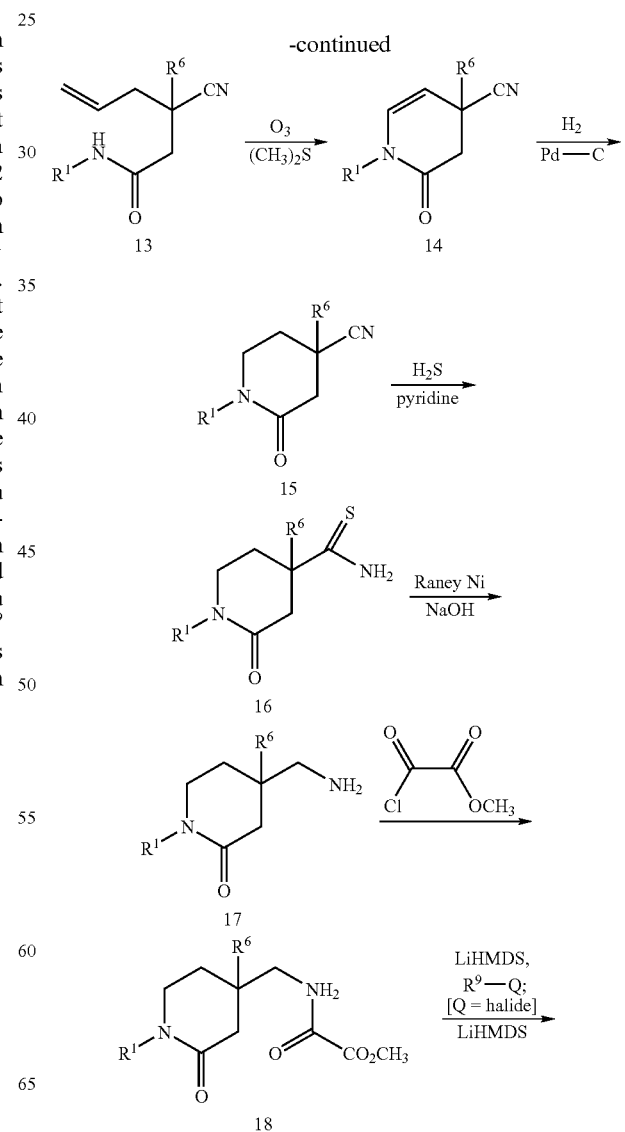

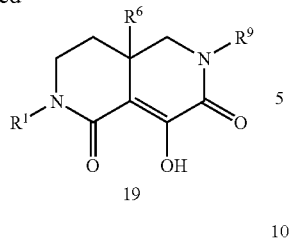

In Scheme 3, an amino compound containing the R[9] variable is alkylated with tert-butyl bromoacetate 20 or an equivalent reagent to give 21. Glycine ester 21 is then acylated with methyl oxalyl chloride or an equivalent reagent to provide 22. Oxalamide 22 is combined with unsaturated lactam 3 in the presence of a strong base such as lithium hexamethyldisilazide which induces a tandem Michael addition and Dieckman-type ring closure to give 2,3,4,4a,5,6-hexahydro-2,6-naphthyridine-1,7-dione 23. The ester group in 23 can then be converted to 2,3,4,4a,5,6-hexahydro-2,6-naphthyridine-1,7-dione amide derivatives 24 in a two-step process involving conversion of the tert-butyl ester to the carboxylic acid using an acid such as trifluoroacetic acid, followed by activation and coupling of the carboxylic acid to an amino compound.

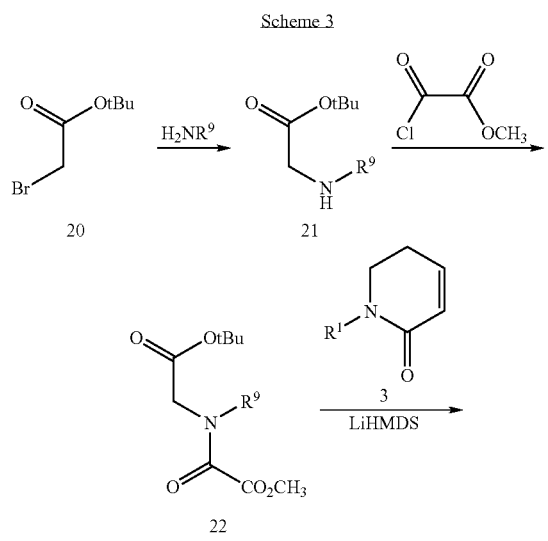

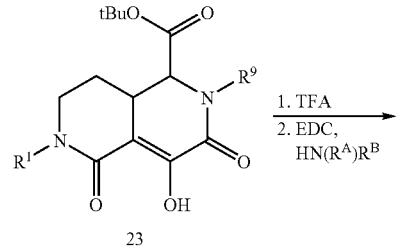

Schemes 4 and 5 show methods to make 2-piperidinones which incorporate R[2] and R[4] substituents on the piperidinone ring. The 2-piperidinone products 28 and 32 in Schemes 4 and 5 can be used as starting materials in place of compound 2 in Scheme 1 to provide 2,3,4,4a,5,6-hexahydro-2,6-naphthyridine-1,7-dione products bearing R[2] and R[4] substituents at positions 3 and 4 on the 2,3,4,4a,5,6-hexahydro-2,6-naphthyridine-1,7-dione ring.

In Scheme 4, delta-keto ester derivative 25 containing the R[2] variable is treated with hydroxylamine to give oxime 26. The oxime group in 26 is converted to an amino group under reducing conditions such as palladium on carbon and hydrogen gas. The resulting amino group then cyclizes onto the ester to form piperidinone 27. Compound 27 is then N-alkylated with a halide compound or an equivalent reagent in the presence of a base such as sodium hydride to give piperidinone 28 which contains the R[1] variable and the R[2] variable at position 6 on the piperidinone ring. Alternatively, the keto group in delta-keto ester derivative 25 is reductively aminated with an amino compound containing the R[1] variable in the presence of a reducing agent such as sodium cyanoborohydride. The resulting amine then cyclizes onto the ester group to give the substituted piperidinone 28.

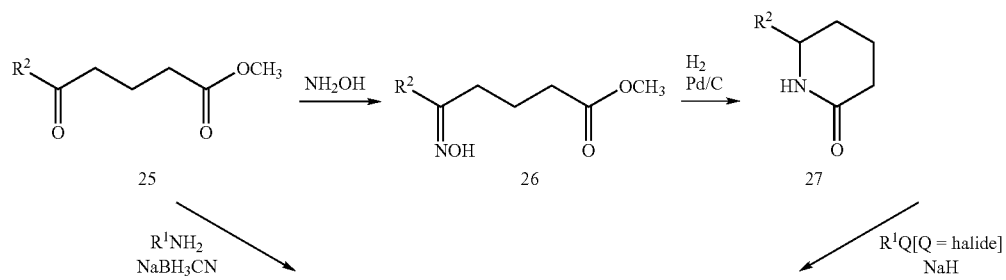

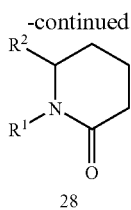

In Scheme 5, nitrile 29 containing the $R^4$ variable is deprotonated with a strong base such as lithium diisopropylamide and the resulting anion undergoes Michael addition to ethyl acrylate or an equivalent reagent to provide 30. The nitrile group in 30 is converted to an amine using reductive conditions such as palladium on carbon and hydrogen gas, and the amine then cyclizes onto the ester to form piperidinone 31. Compound 31 is then N-alkylated with a halide compound or an equivalent reagent in the presence of a base such as sodium hydride to give piperidinone 32 which contains the $R^1$ variable and the $R^4$ variable at position 5 on the piperidinone ring.

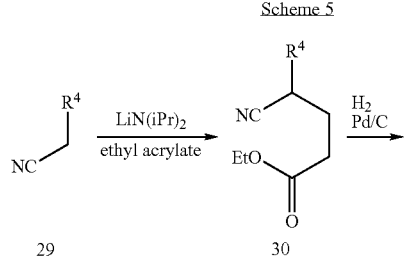

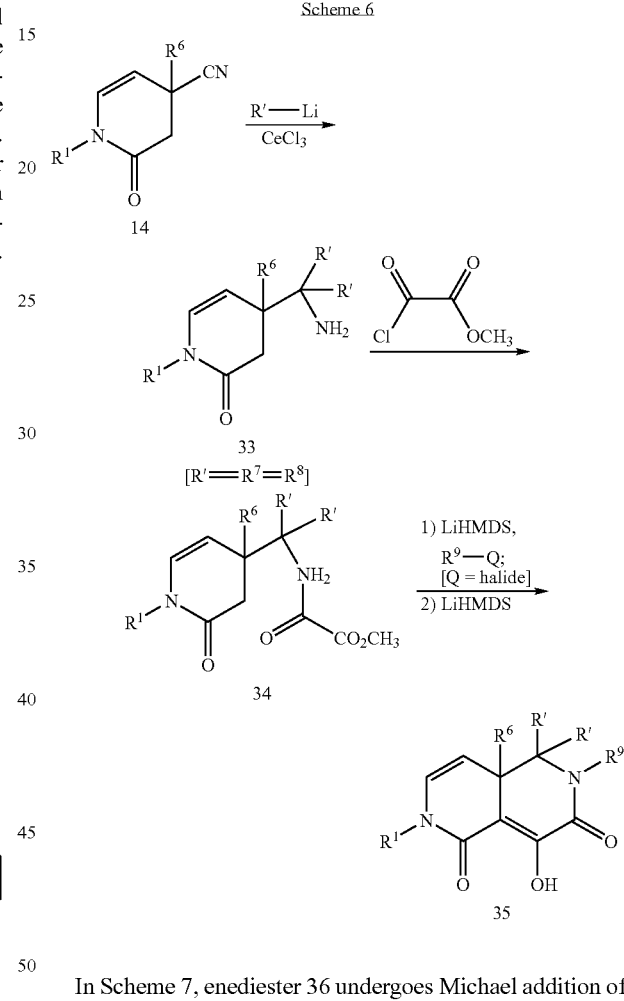

Schemes 6 and 7 present methods for preparing compounds of the present invention which contain 2,4a,5,6-tetrahydro-2,6-naphthyridine-1,7-dione bicyclic nucleus. In Scheme 6, the nitrile group in dihydropyridinone 14 from Scheme 2 is reacted with an organometallic reagent such as an organocerium reagent to introduce $R^7$ and $R^8$ variables and give 33. Amine 33 is acylated with methyl oxalyl chloride or equivalent reagent to give 34. Oxalamide 34 is then treated with a strong base such as lithium hexamethyldisilazide and a halide compound or an equivalent reagent to install the $R^9$ variable, followed by the addition of more strong base such as lithium hexamethyldisilazide to close the ring and furnish 2,4a,5,6-hexahydro-2,6-naphthyridine-1,7-dione 35.

In Scheme 7, enediester 36 undergoes Michael addition of a nitro compound containing the $R^7$ and $R^8$ variables in the presence of a base such as DBU to give 37. The two ester groups in 37 are hydrolyzed to give a diacid, and the diacid is treated with a reagent such as acetic anhydride to close the ring to give 38. Anhydride 38 is then used to acylate an amino compound containing the $R^1$ variable to give an amide acid, treatment of which with a reagent such as EDC closes the ring to give 39. Imide 39 is treated with a reducing agent such as sodium borohydride to form a hydroxy piperidinone which undergoes dehydration upon workup in the presence of an acid such as hydrogen chloride to give dihydropyridinone 40. The nitro group in 40 is reduced with a reagent such as Raney nickel activated with sodium hydroxide to give 41. Amine 41 is acylated with methyl oxalyl chloride or equivalent reagent to give 42. Oxalamide 42 is then treated with a strong base such as lithium hexamethyldisilazide and a halide compound or an equivalent reagent to install the $R^9$ variable, followed by the addition of more strong base such as lithium hexamethyldisilazide to close the ring and provide 2,4a,5,6-hexahydro-2,6-naphthyridine-1,7-dione 43.

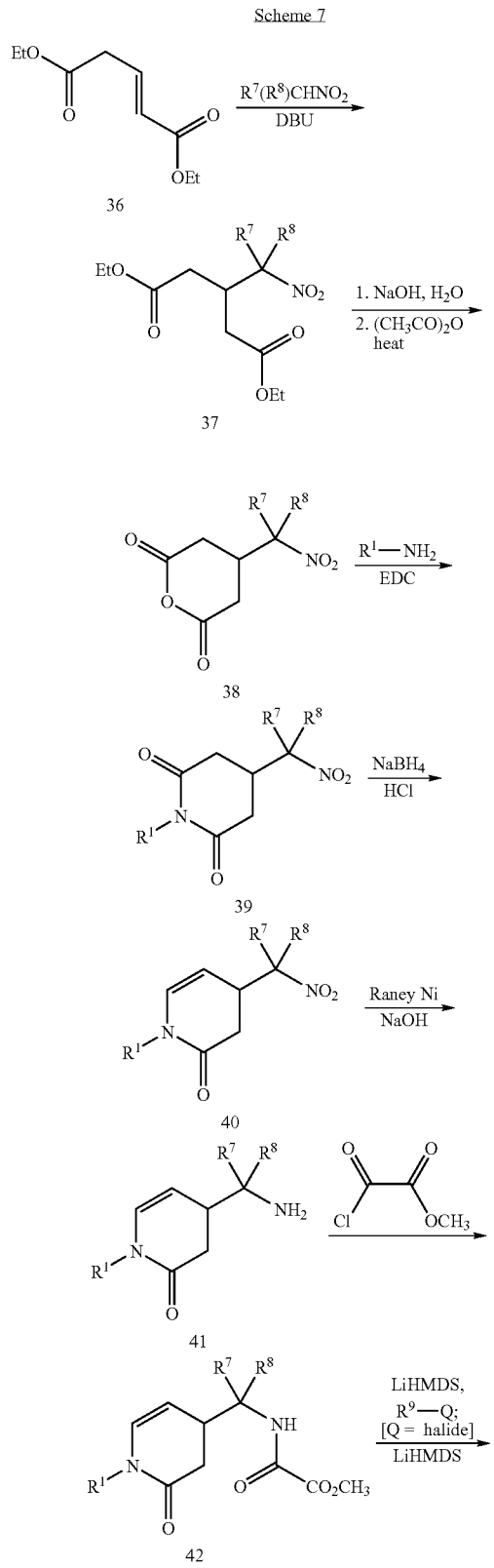

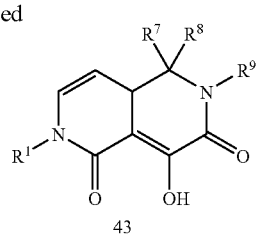

Scheme 8 shows another method for preparing products with changes in the $R^9$ substituent at position 6 on the 2,3,4,4a,5,6-hexahydro-2,6-naphthyridine-1,7-dione ring system. Thus, unsaturated lactam 44 can undergo Michael addition of cyanide, and following treatment of the nitrile with HCl gas in methanol, methyl ester 45 can be obtained. The ester group in 45 can be selectively reduced with a reagent such as lithium borohydride in a solvent such as THF to give alcohol 46. The hydroxyl group in 46 can be converted into a leaving group, for example by formation of a sulfonate ester using a reagent such as methanesulfonyl chloride, and the leaving group can then be readily displaced by an amine to give 47. Amine 47 can then be acylated with a reagent such as ethyl oxalyl chloride to give oxalamide 48. Cyclization of oxalamide 48 to the desired product, 49, can then be accomplished in the presence of a strong base such as LDA.

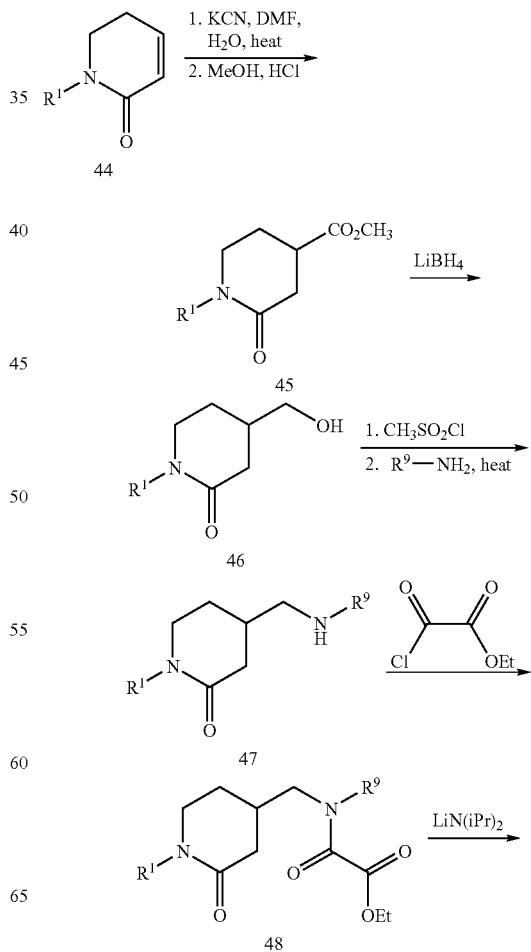

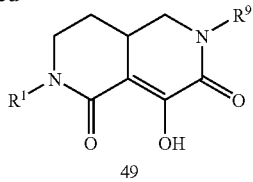

Scheme 9 shows a synthesis of compounds containing the 6,7,8,8a-tetrahydro-1H-pyrano[4,3-c]pyridine-3,5-dione ring system, e.g., 53. Ester 50, the synthesis of which is given in Scheme 8, can be reacted with an organometallic reagent (M-R' wherein M is a metal such as an alkali metal or an alkaline earth metal, and R' is a carbon-based group such as alkyl or substituted alkyl) or metal hydride (R'=H) reagent to give alcohol 51. The hydroxyl group in 51 can be acylated with a reagent such as ethyl oxalyl chloride to give oxalic ester 52. Cyclization of 52 to the desired product, 53, can be accomplished using an amide base such as LDA or LiHMDS, or with an alkoxide base such as tert-butoxide or ethoxide. Alternatively, alcohol 51 can be converted directly to 53 by treatment of 51 with an amide base such as LDA or LiHMDS, or with an alkoxide base such as tert-butoxide or ethoxide, and an oxalate ester such as dimethyl or diethyl oxalate.

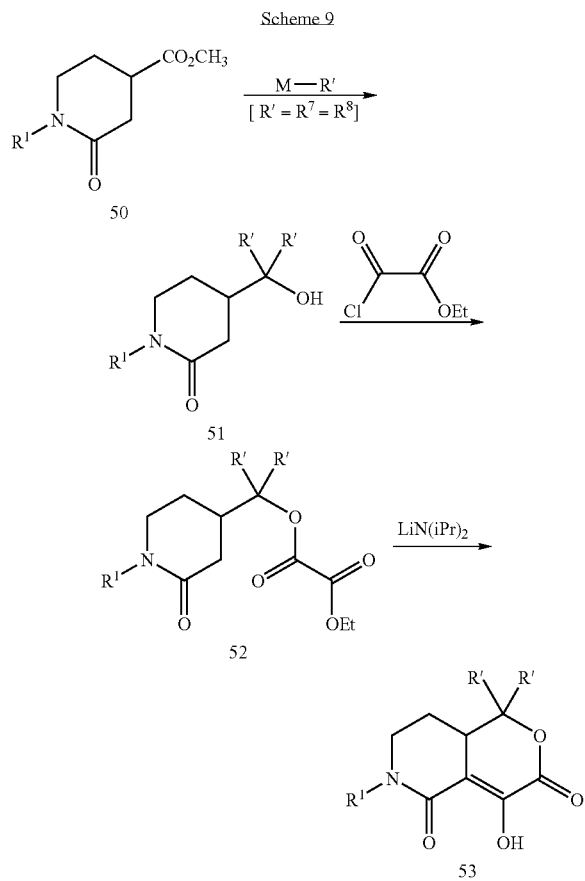

In the processes for preparing compounds of the present invention set forth in the foregoing schemes, functional groups in various moieties and substituents may be sensitive or reactive under the reaction conditions employed and/or in the presence of the reagents employed. Such sensitivity/reactivity can interfere with the progress of the desired reaction to reduce the yield of the desired product, or possibly even preclude its formation. For example, certain functional groups encompassed by R' in Schemes 6 and 9 may be chemically incompatible with the formation of the organometallic reagent M-R'. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, Join Wiley & Sons, 3rd edition, 1999, and 2nd edition, 1991. The protecting groups may be removed at a convenient subsequent stage using methods known in the art. Alternatively the interfering group can be introduced into the molecule subsequent to the reaction step of concern.

The following examples serve only to illustrate the invention and its practice. The examples are not to be construed as limitations on the scope or spirit of the invention.

EXAMPLE 1

2-(4-Fluorobenzyl)-8-hydroxy-6-methyl-2,3,4,4a,5,6-hexahydro-2,6-naphthyridine-1,7-dione

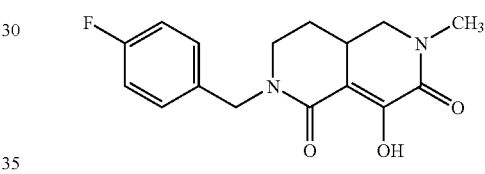

Step 1: 1-(4-Fluorobenzyl)piperidine-2-one

To a solution of 4-fluorobenzyl bromide (15 g, 79 mmol) and 2-piperidinone (8.4 g, 85 mmol) in DMF (150 mL) was added sodium hydride (3.6 g of a 60% suspension in mineral oil, 90 mmol) in portions over a period of 20 min. The mixture was stirred at ambient temperature for 18 hours. The solvent was removed under vacuum and the residue was partitioned between EtOAc and water. The organic extract was washed with brine, dried over $MgSO_4$, filtered, and concentrated under vacuum. The residual oil was purified using silica gel column chromatography eluting with 50%-70% ethyl acetate in hexanes. The appropriate fractions were combined and concentrated to afford the title compound as white solid. $^1$H NMR (400 MHz, $CDCl_3$) δ 7.23 (dd, J=8.7; 5.4 Hz, 2H), 7.00 (t, J=8.7 Hz, 2H), 4.56 (s, 2H), 3.18 (t, J=6 Hz, 2H), 2.46 (t, J=6 Hz, 2H), 1.79 (m, 4H).

Step 2: 1-(4-Fluorobenzyl)-3-(phenylsulfinyl)piperidin-2-one

To a cooled (−20° C.) solution of 1-(4-fluorobenzyl)piperidine (17 g, 82 mmol) in anhydrous THF (200 mL) was added LiHMDS (1.0M in THF, 180 mL, 180 mmol) over a period of 15 min. The reaction mixture was stirred for 30 min at −20° C., then methyl phenylsulfinate (15 g, 98 mmol) was added over a period of 5 min. After being stirred at −20° C. for 1 hour, the reaction was quenched by the addition of water (100 mL). EtOAc (200 mL) was added and the organic layer was separated and washed with water (3×100 mL) and brine.

The organic layer was dried over Mg$_2$SO$_4$, filtered, concentrated under vacuum. The crude product was used without purification in the next step.

Step 3: 1-(4-Fluorobenzyl)-5,6-dihydropyridin-2-(1H)-one

To a stirred solution of 1-(4-fluorobenzyl)-3-(phenylsulfinyl)piperidin-2-one one (25 g, 74 mmol) in toluene (200 mL) was added anhydrous sodium carbonate (20 g, 190 mmol). The mixture was heated to reflux for 1.5 hours. The reaction mixture was cooled to ambient temperature and the solids were removed by filtration. The filtrate solvent was removed under vacuum and the residue was purified using silica gel column chromatography eluting with 3:1 EtOAc:hexanes. Appropriate fractions were combined and removal of the solvents under vacuum gave the title compound as a white solid. $^1$H NMR (400 MHz, CDCl$_3$) δ 7.26 (m, 2H), 7.01 (m, 2H), 6.56 (dt, J=9.9, 4.2 Hz, 1H), 6.00 (dt, J=9.7, 1.8 Hz, 1H), 4.59 (s, 2H), 3.32 (t, J=7.2 Hz, 2H), 2.33 (m, 2H).

Step 4: 1-(4-Fluorobenzyl)-4-(nitromethyl)piperidin-2-one

To a solution of 1-(4-fluorobenzyl)-5,6-dihydropyridin-2-(1H)-one (6.2 g, 30 mmol) in nitromethane (64.5 g, 1.06 mol) under an atmosphere of nitrogen was added DBU (4.59 g, 30.2 mmol). The reaction mixture was stirred overnight at room temperature. The product mixture was concentrated under vacuum. The residue was purified using column chromatography on silica gel eluting with 50%-100% ethyl acetate in hexanes. Collection and concentration of appropriate fractions provided the title compound as pale yellow oil. $^1$H NMR (400 MHz, CDCl$_3$) δ 7.25 (m, 2H), 7.01 (t, J=8.7 Hz, 2H), 4.64 (d, J=14.6 Hz, 1H), 4.48 (d, J=14.5 Hz, 1H), 4.34 (m, 2H), 3.27 (m, 2H), 2.23 (dd, J=17, 10.6 Hz, 1H), 2.0 (m, 1H), 1.61 (m, 1H).

Step 5: 4-(Aminomethyl)-1-(4-fluorobenzyl)piperidin-2-one

To a degassed solution of 1-(4-fluorobenzyl)-4-(nitromethyl)piperidin-2-one (1.4 g, 5.3 mmol) in absolute ethanol (80 mL) was added wet Raney nickel catalyst (1.4 g of a 50% weight slurry in water) which was washed to neutral pH with deionized water and absolute ethanol. The reaction mixture was shaken under an atmosphere of 55 psi of hydrogen for 16 hours. The product mixture was filtered through celite and the filtrate was concentrated under vacuum to afford the title compound as colorless viscous oil. $^1$H NMR (400 MHz, CDCl$_3$) δ 7.24 (m, 2H), 7.01 (t, J=8.7 Hz, 2H), 4.64 (d, J=14.6 Hz, 1H), 4.44 (d, 1H), 3.23 (m, 2H), 2.65 (m, 2H), 2.16-1.28 (m).

Step 6: Ethyl ({[1-4-fluorobenzyl)-2-oxopiperidin-4-yl]methyl}amino)-(oxo)acetate To a cooled (0° C.) solution of 4-(aminomethyl)-1-(4-fluorobenzyl)-piperidin-2-one (1.20 g, 5.07 mmol) in anhydrous methylene chloride (20 mL) under an atmosphere of nitrogen was added diisopropylethylamine (0.72 g, 5.58 mmol). Ethyl oxalyl chloride (0.69 g, 5.07 mmol) was added to the reaction mixture over seven minutes. The reaction stirred at 0° C. for 1 hour, then warmed to room temperature for 2 hours. The resultant solution was diluted with ice water and methylene chloride (100 mL). The organic extract was dried over Na$_2$SO$_4$, filtered, and concentrated under vacuum. The residual oil was purified using column chromatography on silica gel eluting with 20%-80% ethyl acetate in hexanes. Collection and concentration of appropriate fractions provided the title compound as a colorless viscous oil. $^1$H NMR (400 MHz, CDCl$_3$) δ 7.22 (m, 3H), 7.00 (t, J=8.6 Hz, 2H), 4.60 (d, J=14.5 Hz, 1H), 4.49 (d, J=14.5 Hz, 1H), 4.35 (q, J=7.1 Hz, 2H), 3.34-3.15 (m, 4H), 2.61 (m, 1H), 2.15 (m, 2H), 1.92 (m, 1H), 1.51 (m, 1H), 1.39 (t, J=7.1 Hz, 1H).

Step 7: 2-(4-Fluorobenzyl)-8-hydroxy-6-methyl-2,3,4,4a,5,6-hexahydro-2,6-naphthyridine-1,7-dione To a cooled (0° C.) solution of rigorously dried ethyl ({[1-4-fluorobenzyl)-2-oxopiperidin-4-yl]methyl}amino)(oxo)acetate (0.273 g, 0.812 mmol) in anhydrous DMF (1.5 mL) under an atmosphere of nitrogen, was added a solution of LiHMDS in THF (0.85 M, 1 M; 0.85 mmol). The reaction mixture stirred for 30 min at 0° C. Methyl iodide (0.115 g, 0.812 mmol) was added and the mixture was stirred for 2 hours at 0° C., then at room temperature for 16 hours. The reaction was then cooled to 0° C. and treated with a solution of LiHMDS in THF (0.85 mL, 1 M; 0.85 mmol) and stirred for 1 hour at 0° C., then for 20 hours at room temperature. The product mixture was concentrated under vacuum and purified using HPLC on C18 stationary phase eluting with water/acetonitrile/TFA mobile phase. Collection and lyophilization of the appropriate fractions provided the title compound as a white solid. $^1$H NMR (400 MHz, CDCl$_3$) δ 13.66 (br s, 1H), 7.23 (m, 2H), 7.09 (t, J=8.7 Hz, 2H), 4.74 (d, J=14.7 Hz, 1H), 4.46 (d, J=14.7 Hz, 1H), 3.31 (m, 4H), 3.06 (s, 3H), 3.03 (m, 1H), 1.89 (dq, J=13, 3.3 Hz, 1H), 1.55 (qd, J=13, 5.2 Hz, 1H).

EXAMPLE 2

2-(4-Fluorobenzyl)-8-hydroxy-5,5,6-trimethyl-2,3,4,4a,5,6-hexahydro-2,6-naphthyridine-1,7-dione

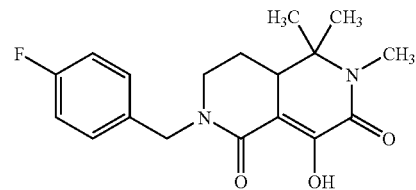

Step 1: 1-(4-Fluorobenzyl)-4-(1-methyl-1-nitroethyl)piperidin-2-one

To a solution 1-(4-fluorobenzyl)-5,6-dihydropyridin-2(1H)-one (see Step 3 of Example 1) (0.75 g, 3.65 mmol) in 2-nitropropane (9.77 g, 109 mmol) was added DBU (0.56 g, 3.65 mmol). After stirring for 48 hours, the reaction mixture was concentrated under vacuum. The residual material was purified using silica gel column chromatography eluting with CH$_2$Cl$_2$. The appropriate fractions were combined and concentrated to afford the title compound. $^1$H NMR (400 MHz, CDCl$_3$) δ 7.44 (m, 2H), 7.04 (t, J=9 Hz, 2H), 4.64 (d, J=15 Hz, 1H), 4.43 (d, J=15 Hz, 1H), 3.23 (m, 2H), 2.56 (m, 2H), 2.22 (m, 1H), 1.73 (m, 1H), 1.56 (s, 6H), 1.51 (m, 1H) ppm. ES MS M+1=295.

Step 2: 4-(1-Amino-1-methylethyl)-1-(4-fluorobenzyl)piperidine-2-one

To a solution of 1-(4-fluorobenzyl)-4-(1-methyl-1-nitroethyl)piperidin-2-one (1.05 g, 3.57 mmol) in degassed ethanol (75 mL) was added Raney Nickel (2 g of a 50% by weight slurry in water). The reaction mixture was shaken under 55 psi of hydrogen fro 4 hours. The reaction mixture was filtered through a bed a celite, then concentrated under vacuum to give an oil that solidified on standing. The solid was triturated in ether and collected by filtration to give the title compound. $^1$H NMR (400 MHz, CDCl$_3$) δ 7.22 (m, 2H), 7.02 (t, J=8.6 Hz, 2H), 4.65 (d, J=14.5 Hz, 1H), 4.44 (d, J=14.6 Hz, 1H), 3.26 (m, 2H), 2.60 (d, J=5 Hz, 1H), 2.25 (m, 1H), 1.97 (d, J=11.5 Hz, 1H), 1.75 (m, 1H), 1.44 (m, 1H), 1.11 (d, J=9 Hz, 6H) ppm. ES MS M+1=265.

Step 3: Ethyl ({1-[1-(4-fluorobenzyl)-2-oxopiperidin-4-yl]-1-methylethyl}amino)(oxo)acetate To a cooled (0° C.) solution of 4-(1-amino-1-methylethyl)-1-(4-fluorobenzyl)piperidine-2-one (0.92 g, 3.5 mmol) and diisopropylethylamine (0.49 g, 3.8 mmol) in CH$_2$Cl$_2$ (10 mL) was added ethyl oxalyl chloride (0.48 g, 3.5 mmol). After stirring at 0° C. for 1 hour, the reaction mixture was partitioned between CH$_2$Cl$_2$ and water. The organic extract was dried with Na$_2$SO$_4$, filtered, and concentrated under vacuum to provide the title compound as an oil. $^1$H NMR (400 MHz, CDCl$_3$) δ 7.22 (m, 2H), 7.01 (m, 2H), 6.93 (br, 1H), 4.59 (d, J=12 Hz, 1H), 4.49 (d, J=12 Hz, 1H), 3.34 (m, 2H), 3.22 (m, 2H), 2.70 (m, 1H), 2.54 (m, 1H), 2.19 (m, 1H), 1.87 (m, 1H), 1.47 (m, 1H), 1.18 (m, 7H), 1.14 (m, 1H) ppm. ES MS M+1=365.

Step 4: 2-(4-Fluorobenzyl)-8-hydroxy-5,5,6-trimethyl-2,3,4,4a,5,6-hexahydro-2,6-naphthyridine-1,7-dione To a cooled (0° C.) solution of ethyl ({1-[1-(4-fluorobenzyl)-2-oxopiperidin-4-yl]-1-methyethyl}amino)(oxo)acetate (1.2 g, 3.3 mmol) in anhydrous DMF (10 mL) under an atmosphere of nitrogen was added LiHMDS (1M in THF, 3.5 mL, 3.5 mmol). After stirring at 0° C. for 15 min, methyl iodide (0.47 g, 3.3 mmol) was added to the reaction mixture. After stirring for an additional 15 min, more LiHMDS (1M in THF, 3.5 mmol, 3.5 mmol) was added. After another 2 h, an additional portion of LiHMDS (1M in THF, 3.5 mL, 3.5 mmol) was added. After stirring at room temperature for 24 hours, the reaction mixture was concentrated under vacuum. The residual material was purified using reverse phase HPLC on a C18 stationary phase eluting with a gradient of 5%-95% acetonitrile (0.1% TFA) in H$_2$O (0.1% TFA) to afford the title compound as an oil $^1$H NMR (400 MHz, CDCl$_3$) δ 7.27 (m, 2H), 7.04 (t, J=8.6 Hz, 2H), 4.67 (d, J=14.7 Hz, 1H), 4.52 (d, J=14.7 Hz, 1H), 3.33 (d, J=6 Hz, 2H), 3.31 (s, 3H), 2.84 (m, 1H), 1.93 (m, 1H), 1.64 (m, 1H), 1.37 (s, 3H), 1.13 (s, 3H) ppm. ES MS M+1=333.

The enantiomers of the title compound were obtained by separation using a ChiralPak AD column with 100% methanol as the mobile phase. On an analytical ChiralPak AD column eluting with 100% methanol, the first enantiomer had a retention time of 5.05 min and a negative sign of rotation the second enantiomer had a retention time of 7.07 min and a positive sign of rotation

EXAMPLE 3

2-(4-Fluorobenzyl)-8-hydroxy-6-methyl-4-a-phenyl-2,3,4,4a,5,6-hexahydro-2,6-naphthyridine-1,7-dione

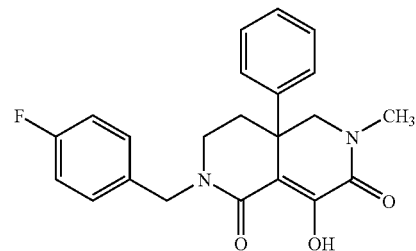

Step 1: 4-Cyano-4-phenyl-1-butene

To a cooled solution (−78° C.) of benzyl cyanide (5.00 g, 42.7 mmol) in anhydrous THF was added LiHMDS (1M in THF, 46.9 mL, 46.9 mmol) dropwise. After 0.5 hour, allyl bromide (5.16 g, 42.6 mmol) was added dropwise to the reaction mixture. The reaction mixture was warmed to room temperature, and the solvent was removed under vacuum. The residual material was purified using silica gel column chromatography eluting with 100% hexanes. The appropriate fractions were combined and concentrated to afford the title compound. $^1$H NMR (400 MHz, DMSO-d$_6$) δ 7.44 (m, 5H), 5.81 (m, 1H), 5.12 (m, 2H), 4.35 (t, J=6.9 Hz, 1H), 2.61 (m, 2H) ppm. ES MS M+1=158.

Step 2: Methyl 3-cyano-3-phenylhex-5-enoate

To a cooled solution (−78° C.) of 4-cyano-4-phenyl-1-butene (6.23 g, 39.6 mmol) in anhydrous THF was added LIDS (1M in THF, 43.5 mL, 43.5 mmol) dropwise. The solution was stirred at −78° C. for 0.5 hour, then methyl bromoacetate (6.67 g, 43.6 mmol) was added dropwise. After stirring at room temperature for 24 hours, the reaction mixture was concentrated under vacuum. The residual material was purified using silica gel column chromatography eluting with 0-20% EtOAc in hexanes. The appropriate fractions were combined and concentrated to afford the title compound. $^1$H NMR (400 MHz, DMSO-d$_6$) δ 7.38 (m, 5H), 5.57 (m, 1H), 5.14 (m, 2H), 3.49 (s, 3H), 3.49 (m, 2H), 2.78 (m, 2H) ppm. ES MS M+1=230.

Step 3: 3-Cyano-3-phenylhex-5-enoic acid

To a solution of methyl 3-cyano-3-phenylhex-5-enoate (6.03 g, 26.3 mmol) in methanol (90 mL) was added 1M aqueous NaOH (29 mL, 29 mmol). After stirring overnight at room temperature, the reaction mixture was concentrated under vacuum. The residue was partitioned between EtOAc and water and the pH of the aqueous phase was adjust to pH 4 using 3N aqueous HCl. The organic extract was dried with Na$_2$SO$_4$, filtered, and concentrated under vacuum to provide the title compound as a yellow oil. $^1$H NMR (400 MHz, DMSO-d$_6$) δ 12.45 (br, 1H), 7.50 (d, J=1.6 Hz, 2H), 7.45 (t, J=1.9 Hz, 2H) 7.42 (t, J=1.7 Hz, 1H), 5.51 (m, 1H), 5.11 (m, 2H), 3.17 (s, 2H), 2.77 (m, 2H), 2.51 (s, 2H) ppm. ES MS M+1=216.

Step 4: 3-Cyano-N-(4-fluorobenzyl)-3-phenylhex-5-enamide

To a solution f 3-cyano-3-phenylhex-5-enoic acid (5.66 g, 26.3 mmol) and 4-fluorobenzylamine (3.95 g, 31.6 mmol) in DMF was added 1-hydroxybenzotriazole hydrate (6.04 g, 39.4 mmol), 1-(3-dimethylaminopropyl)-3-ethylcarbodiimide hydrochloride (7.56 g, 39.4 mmol), and triethylamine (3.19 g, 31.5 mmol). After stirring overnight at room temperature, the reaction mixture was concentrated under vacuum. The residue was partitioned between EtOAc and water. The organic extract was dried with $Na_2SO_4$, filtered, and concentrated under vacuum to provide the title compound as a light yellow solid. $^1$H NMR (400 MHz, DMSO-$d_6$) δ 8.41 (s, 1H), 7.47 (d, J=7.9 Hz, 2H), 7.36 (t, J=7 Hz, 2H) 7.35 (t, J=7 Hz, 1H), 7.04 (t, J=8.9 Hz, 2H), 6.97 (t, J=8.6 Hz, 2H), 5.53 (m, 1H), 5.12 (m, 2H), 4.21 (m, 1H), 4.08 (m, 1H), 2.88 (m, 3H), 2.77 (m, 1H) ppm. ES MS M+1=323.

Step 5: 4-Cyano-1-(4-fluorobenzyl)-4-phenyl-1,2,3,4-tetrahydropyridin-2-one

Into a cooled (−78° C.) solution of 3-cyano-N-(4-fluorobenzyl)-3-phenylhex-5-enamide (8.00 g, 24.8 mmol) in $CH_2Cl_2$ (500 mL) was bubbled ozone until a blue color persisted. The mixture was stirred for 10 min, then dimethyl sulfide (84.6 g, 1.36 mol) was added. After stirring for 48 hours at room temperature, the mixture was concentrated under vacuum. The residue was partitioned between EtOAc and water. The organic extract was dried with $Na_2SO_4$, filtered, and concentrated under vacuum. The residual material was purified using silica gel column chromatography eluting with 0-40% EtOAc in hexanes. The appropriate fractions were combined and concentrated to afford the title compound. $^1$H NMR (400 MHz, DMSO-$d_6$) δ 7.45 (m, 5H), 7.29 (m, 2H), 7.15 (t, J=8.9 Hz, 2H), 6.78 (d, J=7.7 Hz, 1H), 5.50 (d, J=7.7 Hz, 1H), 4.72 (s, 2H), 3.17 (q, J=16 Hz, 2H) ppm. ES MS M+1=307.

Step 6: 4-Cyano-1-(4-fluorobenzyl)-4-phenylpiperidin-2-one

To a solution of 4-cyano-1-(4-fluorobenzyl)-4-phenyl-1,2,3,4-tetrahydropyridin-2-one (3.98 g, 13.0 mmol) in degassed methanol was added 10% Pd/C (0.8 g). The reaction shaken under an atmosphere of 33 psi of hydrogen for 18 hours. More 10% Pd/C (0.4 g) was added and the mixture was shaken under 45 psi of hydrogen for 48 hours. The mixture was filtered through a bed of celite and the filtrate was concentrated to give the title compound as a white solid. $^1$H NMR (400 MHz, DMSO-$d_6$) δ 7.55 (d, J=7.7 Hz, 2H), 7.46 (t, J=7.9 Hz, 2H), 7.38 (t, J=7.3 Hz, 1H), 7.28 (t, J=3 Hz, 2H), 7.16 (t, J=2.4 Hz, 2H), 4.58 (s, 2H), 3.44 (m, 1H), 3.25 (m, 1H), 3.07 (q, J=16 Hz, 2H), 2.41 (s, 2H) ppm. ES MS M+1=309.

Step 7: 1-(4-Fluorobenzyl)-4-phenylpiperidin-2-one-4-carbothioamide

To a cooled (0° C.) solution of 4-cyano-1-(4-fluorobenzyl)-4-phenylpiperidin-2-one (3.39 g, 10.9 mmol) in pyridine (77 mL) was added triethylamine (45.0 g, 0.77 mol). The reaction mixture was saturated with hydrogen sulfide gas, the reaction vessel was sealed and then brought to ambient temperature. After stirring for 24 hours, the reaction mixture was cooled (0° C.), the reaction vessel was opened, then the solvents were concentrated under vacuum. The residual material was purified using silica gel column chromatography eluting with 0-70% EtOAc in hexanes. The appropriate fractions were combined and concentrated to afford the title compound. $^1$H NMR (400 MHz, DMSO-$d_6$) δ 9.65 (s, 1H), 8.68 (s, 1H), 7.35 (m, 4H), 7.26 (t, J=7 Hz, 1H), 7.13 (t, J=8.3 Hz, 2H), 7.04 (t, J=8.9 Hz, 2H), 4.48 (d, J=15 Hz, 1H), 4.35 (d, J=15 Hz, 1H), 3.16 (m, 2H), 3.93 (d, J=17 Hz, 1H), 2.82 (m, 1H), 2.51 (m, 2H) ppm. ES MS M+1=343.

Step 8: 4-Aminomethyl-1-(4-fluorobenzyl)-4-phenylpiperidin-2-one

To a solution of Raney nickel (50% by weight slurry in water, 0.66 g, 11.3 mmol) in ethanol was added sodium hydroxide (0.45 g, 11.3 mmol) and the mixture was heated to 50° C. under an atmosphere of nitrogen. After 0.5 hour, 1-(4-fluorobenzyl)-4-phenylpiperidin-2-one-4-carbothioamide (1.94 g, 5.66 mmol) in ethanol (5 mL) was added and the reaction mixture was stirred at 50° C. for 1.5 hours. The solids were then removed by filtration through celite and the filtrate was concentrated under vacuum. The residual material was purified using reverse phase HPLC on a C18 stationary phase eluting with a gradient of 5%-95% acetonitrile (0.1% TFA) in $H_2O$ (0.1% TFA) to afford the TFA salt of the title compound as a white solid. $^1$H NMR (400 MHz, DMSO-$d_6$) δ 7.61 (br, 2H), 7.39 (m, 5H), 6.97 (m, 4H), 4.61 (d, J=15 Hz, 1H), 4.13 (d, J=15 Hz, 1H), 3.12 (m, 4H), 2.67 (d, J=7 Hz, 1H), 2.51 (m, 1H), 2.23 (m, 1H), 2.18 (m, 1H) ppm. ES MS M+1=313.

Step 9: Ethyl ({[1-fluorobenzyl)-2-oxo-4-phenylpiperidin-4-yl}methyl}amino)(oxo)acetate To a cooled (0° C.) solution of 4-(aminomethyl)-1-(4-fluorobenzyl)-4-phenylpiperidin-2-one (0.40 g, 1.28 mmol) in $CH_2Cl_2$ was added diisopropylethylamine (0.19 g, 1.53 mmol) and ethyl oxalyl chloride (0.19 g, 1.41 mmol). After 1 hour, the reaction mixture was concentrated. The residual material was purified using reverse phase HPLC on a C18 stationary phase eluting with a gradient of 5%-95% acetonitrile (0.1% TFA) in $H_2O$ (0.1% TFA) to afford the title compound as a white solid. $^1$H NMR (400 MHz, DMSO-$d_6$) δ 8.67 (m, 1H), 7.34 (m, 5H), 6.95 (m, 4H), 4.58 (d, J=15 Hz, 1H), 4.21 (q, J=7 Hz, 2H), 4.11 (d, J=15 Hz, 1H), 3.38 (m, 1H), 3.28 (m, 1H), 3.09 (m, 1H), 2.83 (d, J=17 Hz, 1H), 2.56 (d, J=13 Hz, 2H), 2.21 (m, 1H), 1.98 (m, 1H), 1.25 (t, J=7 Hz, 3H) ppm. ES MS M+1=413.

Step 10: 2-(4-Fluorobenzyl)-8-hydroxy-6-methyl-4-a-phenyl-2,3,4,4a,5,6-hexahydro-2,6-naphthyridine-1,7-dione To a cooled (0° C.) solution of ethyl ({[1-fluorobenzyl)-2-oxo-4-phenylpiperidin-4-yl}methyl}amino)(oxo)acetate (0.27 g, 0.65 mmol) in DMF was added LiHMDS (0.71 mL of a 1.0 M solution in THF, 0.71 mmol) and iodomethane (0.34 g, 2.01 mmol). After stirring at room temperature under anhydrous conditions for 6 hours, the reaction was cooled to 0° C. and more LiHMDS (1.94 mmol) was added. After stirring overnight at room temperature, the reaction mixture was filtered and concentrated. The residual material was purified using reverse phase HPLC on a C18 stationary phase eluting with a gradient of 5%-95% acetonitrile (0.1% TFA) in $H_2O$ (0.1% TFA) to give a solid which was crystallized from methanol to afford the title compound. $^1$H NMR (400 MHz, DMSO-$d_6$) δ 7.31 (m, 7H), 7.15 (m, 2H), 4.66 (d, J=3.3 Hz, 1H), 4.63 (d, J=3.2 Hz, 1H), 3.85 (d, J=3.7 Hz, 1H), 3.82 (d, J=3.5 Hz, 1H), 3.17 (d, J=12 Hz, 1H), 2.68 (s, 3H), 2.55 (m, 1H), 2.16 (d, J=1 Hz, 1H), 1.98 (m, 1H) ES MS M+1=381.

The enantiomers of the title compound were separated using a ChiralPak AD column with 50% methanol in ethanol as the mobile phase. On an analytical ChiralPak AD column eluting with 50% methanol in ethanol, the first enantiomer had a retention time of 5.92 min and a negative sign of rotation, the second enantiomer had a retention time of 8.98 min and a positive sign of rotation.

EXAMPLE 4

5-(tert-Butyloxycarbonyl)-2-(4-fluorobenzyl)-8-hydroxy-6-methyl-2,3,4,4a,5,6-hexahydro-2,6-naphthyridine-1,7-dione

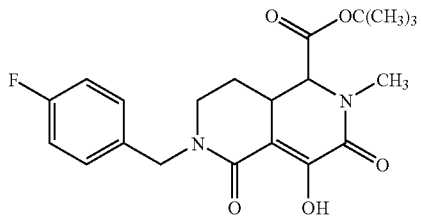

Step 1: tert-Butyl N-[ethoxy(oxo)acetyl]-N-methylglycinate

To a solution tert-butyl N-methylglycinate hydrochloride (1.82 g, 10.0 mmol) in 1,2-dichloroethane (15 mL) was added triethylamine (2.13 g, 21.0 mmol). After stirring for 0.5 hour at room temperature, the reaction mixture was cooled to 0° C. and ethyl oxalyl chloride (1.44 g, 10.5 mmol) was added dropwise over 10 min. After warming to room temperature and stirring for 24 hours, the reaction mixture was partitioned between 1,2-dichloroethane and water. The organic extract was dried with $Na_2SO_4$, filtered, and concentrated under vacuum to provide the title compound as a yellow oil. $^1$H NMR (300 MHz, $CDCl_3$) δ 4.32 (m, 2H), 4.03 (d, J=3.9 Hz, 2H), 3.06 (d, J=10.3 Hz, 3H), 1.48 (s, 9H), 1.38 (m, 3H) ppm. ES MS M+1=246.

Step 2: 5-(tert-Butyloxycarbonyl)-2-(4-fluorobenzyl)-8-hydroxy-6-methyl-2,3,4,4a,5,6-hexahydro-2,6-naphthyridine-1,7-dione To a cooled (−78° C.) solution of tert-butyl N-[ethoxy(oxo)acetyl]-N-methylglycinate (1.43 g, 5.85 mmol) and 1-(4-fluorobenzyl)-5,6-dihydropyridin-2(1H)-one from Step 3 of Example 1 (1 g, 5 mmol) in anhydrous THF (10 mL) was added LiHMDS (1 M in THF) (1.02 g, 6.09 mmol) dropwise. The reaction mixture was stirred for 10 min. at −78° C., warmed to room temperature for 2.5 hours, then heated to 40° C. After heating for 24 hours, the reaction mixture was quenched with cold diluted HCl, then diluted with methanol, and concentrated under vacuum. The residual material was purified using reverse phase HPLC on a C18 stationary phase eluting with 5%-95% acetonitrile (0.1% TFA) in $H_2O$ (0.1% TFA) to give the title compound as a mixture of diastereomers. The appropriate fractions were collected for the first-eluting diastereomer, diastereomer 1, and this material was purified further using reverse phase HPLC on a C18 stationary phase eluting with 15%-85% acetonitrile (0.1% TFA) in $H_2O$ (0.1% TFA). For the second eluting diastereomer, diastereomer 2, the appropriate fractions were collected and the material was purified further using reverse phase HPLC on a C18 stationary phase eluting with 10%-60% methanol (0.1% TFA) in $H_2O$ (0.1% TFA). Diastereomer 1, the hydrogens at positions 4a and 5 have a trans relationship to one another: $^1$H NMR (400 MHz, $CDCl_3$) δ 6.84 (m, 2H), 6.62 (t, J=8.7 Hz, 2H), 4.31 (d, J=14.7 Hz, 1H), 4.05 (d, J=14.7 Hz, 1H), 3.43 (d, J=6.5 Hz, 1H), 2.91 (m, 2H), 2.69 (m, 1H), 2.57 (s, 3H), 1.42 (m, 1H), 1.21 (m, 1H), 1.15 (s, 9H) ppm. ES MS M+1=405. Diastereomer 2, the hydrogens at positions 4a and 5 have a cis relationship to one another: $^1$H NMR (400 MHz, $CDCl_3$) δ 13.07 (s, 1H), 7.22 (m, 2H), 7.02 (t, J=8.7 Hz, 2H), 4.67 (d, J=14.7 Hz, 1H), 4.51 (d, J=14.7 Hz, 1H), 3.82 (d, J=6.5 Hz, 1H), 3.33 (m, 1H), 2.99 (s, 3H), 2.02 (m, 3H), 1.68 (m, 1H), 1.44 (s, 9H) ppm. ES MS M+1=405.

EXAMPLE 5

5-Ethyl-2-(4-fluorobenzyl)-8-hydroxy-6-methyl-2,3,4,4a,5,6-hexahydro-2,6-naphthyridine-1,7-dione

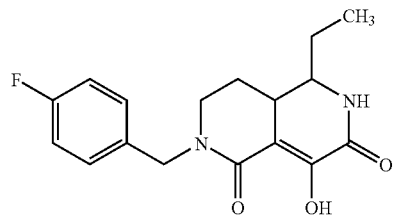

Step 1: 1-(4-Fluorobenzyl)-4-(1-nitropropyl)piperidin-2-one

To a solution 1-(4-fluorobenzyl)-5,6-dihydropyridin-2 (1H)-one (2.0 g, 10 mmol) in 1-nitropropane (8.68 g, 97.5 mmol) was added DBU (1.48 g, 9.75 mmol). After stirring for 24 hours, the reaction mixture was concentrated under vacuum. The residual material was purified by silica gel column chromatography eluting with 1% methanol in $CH_2Cl_2$. The appropriate fractions were combined and concentrated to afford the title compound as mixture of diastereomers. The diastereomers co-eluted with a retention time of 3.01 min. The HPLC method was performed on a Hewlett-Packard Zorbax SB-C8 column (75×4.6 mm, 3.5 micron) eluting with 5%-100% $CH_3CN$ (0.1% TFA) in $H_2O$ (0.1% TFA). ES MS M+1=295.

Step 2: 4-(1-Aminopropyl)-1-(4-fluorobenzyl)piperidin-2-one

To a solution of 1-(4-fluorobenzyl)-4-(1-nitropropyl)piperidin-2-one (2.8 g, 9.51 mmol) in ethanol (50 mL) was added Raney Nickel (2 grams of a 50% by weight slurry in water). The reaction mixture was shaken under 55 psi of hydrogen. After 24 hours, the reaction mixture was filtered through a bed a celite, then concentrated under vacuum to afford the title compound as a mixture of diastereomers. The first diastereomer has a retention time of 2.05 min and the second diastereomer has a retention time of 2.10 min. The HPLC method was performed on a Hewlett-Packard Zorbax SB-C8 column (75×4.6 mm, 3.5 micron) eluting with 5%-100% $CH_3CN$ (0.1% TFA) in $H_2O$ (0.1% TFA). ES MS M+1=265.

Step 3: 5-Ethyl-2-(4-fluorobenzyl)-8-hydroxy-2,3,4,4a,5,6-hexahydro-2,6-naphthyridine-1,7-dione To a cooled (−78° C.) solution of 4-(1-aminopropyl)-1-(4-fluorobenzyl)piperidin-2-one (2.0 g, 8 mmol) in anhydrous THF (20 mL) was added LiHMDS (1M in THF, 18.9 mL, 18.9 mmol) under an atmosphere of nitrogen. After stirring at −78° C. for 5 min, diethyl oxalate (3.32 g, 22.7 mmol) was added to the reaction mixture. After stirring for 2 hours at −78° C., then for 0.5 hour at −20° C., LiHMDS (1M in THF, 22 mL, 22 mmol) was added. After stirring at room temperature for 24 hours, the reaction mixture was quenched with 1N HCl. The mixture was partitioned between EtOAc and water. The organic extract was dried with $Na_2SO_4$, filtered, concentrated under vacuum, then filtered through a plug of silica gel and eluting with 1% methanol in $CH_2Cl_2$. The diastereomers were separated using reverse phase HPLC on a C18 stationary phase eluting with 5%-95% acetonitrile (0.1% TFA) in $H_2O$ (0.1% TFA) to afford the title compounds. Diastereomer 1, the hydrogens at positions 4a and 5 have a cis relationship to one another: $^1H$ NMR (400 MHz, $CDCl_3$) δ 13.67 (br, 1H), 7.26 (m, 2H), 7.04 (t, J=8.6 Hz, 2H), 4.68 (d, J=14.7 Hz, 1H), 4.52 (d, J=14.7 Hz, 1H), 3.35 (m, 4H), 1.79 (m, 3H), 1.48 (m, 1H), 0.97 (t, J=7.3 Hz, 3H) ppm. ES MS M+1=319. Diastereomer 2, the hydrogens at positions 4a and 5 have a trans relationship to one another: $^1H$ NMR (400 MHz, $CDCl_3$) δ 7.26 (m, 2H), 7.04 (t, J=8.6 Hz, 2H), 6.54 (br, 1H), 4.72 (d, J=14.7 Hz, 1H), 4.49 (d, J=14.7 Hz, 1H), 3.34 (m, 3H), 2.73 (dt, J=4, 13 Hz, 1H), 1.99 (m, 1H), 1.78 (m, 1H), 1.57 (m, 2H), 1.01 (t, J=7.5 Hz, 3H) ppm. ES MS M+1=319.

EXAMPLE 6

(Cis-4a,5)-5-Ethyl-2-(4-fluorobenzyl)-8-hydroxy-6-methyl-2,3,4,4a,5,6-hexahydro-2,6-naphthyridine-1,7-dione

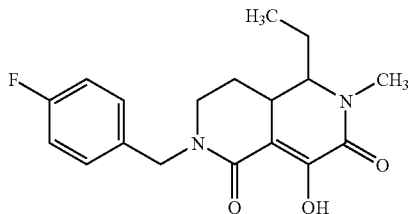

Step 1: (Cis-4a,5)-5-Ethyl-2-(4-fluorobenzyl)-8-methoxy-6-methyl-2,3,4,4a,5,6-hexahydro-2,6-naphthyridine-1,7-dione To a solution of 5-ethyl-2-(4-fluorobenzyl)-8-hydroxy-2,3,4,4a,5,6-hexahydro-2,6-naphthyridine-1,7-dione, Diastereomer 1 from Example 5 (0.46 g, 1.5 mmol) in THF (30 mL) was added cesium carbonate (1.4 g, 4.3 mmol) and methyl iodide (1.02 g, 7.19 mmol). After stirring for 24 hours at room temperature, the reaction mixture was partitioned between EtOAc and 1N HCl. The organic extract was dried with $Na_2SO_4$, filtered, and concentrated under vacuum. The residual material was purified using reverse phase HPLC on a C18 stationary phase eluting with 5%-95% acetonitrile (0.1% TFA) in $H_2O$ (0.1% TFA) to afford the title compound as a yellow oil. $^1H$ NMR (400 MHz, $CDCl_3$) δ 7.51 (m, 2H), 7.05 (t, J=9 Hz, 2H), 5.12 (d, J=15 Hz, 1H), 4.73 (d, J=15 Hz, 1H), 4.56 (d, J=15 Hz, 1H), 4.17 (d, J=15 Hz, 1H), 3.28 (m, 3H), 3.13 (d, J=15 Hz, 3H), 2.39 (m, 1H), 2.18 (m, 1H), 1.67 (m, 4H), 0.98 (s, 3H) ppm. ES MS M+1=347.

Step 2: (Cis-4a,5)-5-Ethyl-2-(4-fluorobenzyl)-8-hydroxy-6-methyl-2,3,4,4a,5,6-hexahydro-2,6-naphthyridine-1,7-dione To a cooled (0° C.) solution of 5-ethyl-2-(4-fluorobenzyl)-8-methoxy-6-methyl-2,3,4,4a,5,6-hexahydro-2,6-naphthyridine-1,7-dione (0.26 g, 0.75 mmol) in $CH_2Cl_2$ (20 mL) was added boron tribromide (0.94 g, 3.8 mmol). After stirring for 0.5 hour at 0° C., the reaction mixture was quenched with methanol, then concentrated under vacuum. The residual material was purified using reverse phase HPLC on a C18 stationary phase eluting with 5%-95% acetonitrile (0.1% TFA) in $H_2O$ (0.1% TFA) to afford the title compound. $^1H$ NMR (400 MHz, $CDCl_3$) δ 7.24 (m, 2H), 7.05 (t, J=9 Hz, 2H), 5.12 (d, J=14.6 Hz, 1H), 4.73 (d, J=14.7 Hz, 1H), 3.14 (s, 3H), 1.76 (m, 4H), 0.98 (t, J=7.5 Hz, 3H) ppm. ES MS M+1=333.

EXAMPLE 7

(Trans-4a,5)-5-Ethyl-2-(4-fluorobenzyl)-8-hydroxy-6-methyl-2,3,4,4a,5,6-hexahydro-2,6-naphthyridine-1,7-dione

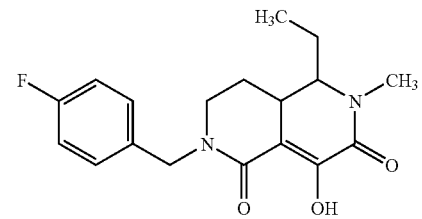

Step 1: (Trans-4a,5)-5-Ethyl-2-(4-fluorobenzyl)-8-methoxy-6-methyl-2,3,4,4a,5,6-hexahydro-2,6-naphthyridine-1,7-dione The title compound was prepared from 5-ethyl-2-(4-fluorobenzyl)-8-hydroxy-2,3,4,4a,5,6-hexahydro-2,6-naphthyridine-1,7-dione, Diastereomer 2 from Example 5, using the procedure given in Step 1 of Example 6. ES MS M+1=347.

Step 2: (Trans-4a,5)-5-Ethyl-2-(4-fluorobenzyl)-8-hydroxy-6-methyl-2,3,4,4a,5,6-hexahydro-2,6-naphthyridine-1,7-dione To a cooled (0° C.) solution of 5-ethyl-2-(4-fluorobenzyl)-8-methoxy-6-methyl-2,3,4,4a,5,6-hexahydro-2,6-naphthyridine-1,7-dione, (0.39 g, 1.1 mmol) in $CH_2Cl_2$ (20 mL) was added hydrogen bromide (30% in HOAc, 5 mL). After stirring for 3 hours at 0° C., the reaction mixture was concentrated under vacuum. The residual material was purified using reverse phase HPLC on a C18 stationary phase eluting with 5%-95% acetonitrile (0.1% TFA) in H₂O (0.1% TFA) to afford the title compound. ¹H NMR (400 MHz, CDCl₃) δ 13.73 (s, 1H), 7.26 (m, 2H), 7.04 (t, J=9 Hz, 2H), 4.69 (d, J=14.6 Hz, 1H), 4.49 (d, J=14.7 Hz, 1H), 3.36 (m, 3H), 3.04 (s, 3H), 2.83 (dt, J=12.3; 4.2 Hz, 1H), 1.97 (m, 2H), 1.68 (m, 2H), 0.92 (t, J=7.3 Hz, 3H) ppm. ES MS M+1=333.

EXAMPLE 8

6-(Cyclopropylmethyl)-2-(4-fluorobenzyl)-8-hydroxy-5,5-dimethyl-2,3,4,4a,5,6-hexahydro-2,6-naphthyridine-1,7-dione

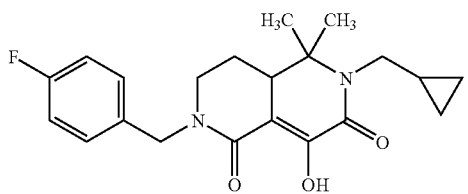

Step 1: 4-{1-[(Cyclopropylmethyl)amino]-1-methyethyl}-1-(4-fluorobenzyl)piperidin-2-one To a suspension of 4-(1-amino-1-methyethyl)-1-(4-fluorobenzyl)piperidin-2-one from Example 2, Step 2, (1.00 g, 3.78 mmol) in acetonitrile (20 mL) was added cesium carbonate (2.46 g, 7.56 mmol) and bromomethylcyclopropane (1.02 g, 7.56 mmol). After stirring at room temperature for 48 hours, more bromomethylcyclopropane (0.36 g, 2.67 mmol) was added. After 24 hours, more bromomethylcyclopropane (0.36 g, 2.67 mol) was added. After another 24 hours, the product mixture was concentrated. The residue was partitioned between ethyl acetate and H₂O. The organic extract was washed with brine, dried with Na₂SO₄, filtered, and concentrated under vacuum. The residual material was purified using reverse phase HPLC on a C18 stationary phase eluting with a gradient of 5%-95% acetonitrile (0.1% TFA) in H₂O (0.1% TFA) to afford the title compound as the TFA salt. The TFA salt was dissolved in saturated NaHCO₃ and extracted with EtOAc. The combined organic extract was dried over Na₂SO₄, filtered, and concentrated under vacuum to give the free base of the title compound. ¹H NMR (400 MHz, CDCl₃) δ 7.21 (m, 2H), 7.01 (t, J=10 Hz, 2H), 4.64 (d, J=16 Hz, 1H), 4.46 (d, J=16 Hz, 1H), 3.24 (m, 1H), 3.15 (m, 1H), 2.55 (m, 1H), 2.34 (d, J=6.8 Hz, 2H), 2.24 (m, 1H), 1.94 (m, 1H), 1.81 (m, 1H), 1.46 (m, 1H), 1.01 (s, 6H), 0.86 (m, 1H), 0.45 (d, J=1.1 Hz, 2H), 0.082 (t, J=5.9 Hz, 2H) ppm. ES MS M+1=319.

Step 2: Ethyl ((cyclopropylmethyl){1-[1-(4-fluorobenzyl)-2-oxopiperidin-4-yl]-1-methylethyl}amino)(oxo)acetate To a solution of 4-{1-[(cyclopropylmethyl)amino]-1-methyethyl}-1-(4-fluorobenzyl)piperidin-2-one (1.4 g, 4.4 mmol) in CH₂Cl₂ (15 mL) was added DIEA (0.625 g, 4.83 mmol) and ethyl oxalyl chloride (0.6 g, 4.4 mmol). After 1.5 hours, the reaction mixture was partitioned between CH₂Cl₂ and water. The organic extract was washed with brine, dried with Na₂SO₄, filtered, and concentrated under vacuum. The residue was purified by silica gel column chromatography eluting with 1-3% methanol in CH₂Cl₂. The appropriate fractions were combined and concentrated to afford the title compound. ¹H NMR (400 MHz, CDCl₃) δ 7.22 (m, 2H), 7.01 (t, J=8 Hz, 2H), 4.68 (d, J=16 Hz, 1H), 4.38 (d, J=16 Hz, 1H), 4.30 (q, J=8 Hz, 2H), 3.34 (m, 1H), 3.19 (m, 4H), 2.56 (m, 1H), 2.21 (m, 1H), 1.82 (m, 1H), 1.49 (s, 3H), 1.44 (m, 1H), 1.41 (s, 3H), 1.35 (q, J=7 Hz, 3H), 1.01 (m, 1H), 0.61 (m, 2H), 0.25 (m, 2H) ppm. ES MS M+1=419.

Step 3: 6-(Cyclopropylmethyl)-2-(4-fluorobenzyl)-8-hydroxy-5,5-dimethyl-2,3,4,4a,5,6-hexahydro-2,6-naphthyridine-1,7-dione To a cooled solution (0° C.) of ethyl ((cyclopropylmethyl){1-[1-(4-fluorobenzyl)-2-oxopiperidin-4-yl]-1-methylethyl}amino)(oxo)acetate (1.56 g, 3.73 mmol) in DMF (15 mL) was added LiHMDS (1M in THF, 5.59 mL, 5.59 mmol) dropwise over 1 min. After stirring for 3 hours, the product mixture was concentrated under vacuum and purified using reverse phase HPLC on C18 stationary phase eluting with a gradient of 5%-95% acetonitrile (0.1% TFA) in H₂O (0.1% TFA) to afford the title compound as a pale yellow solid. ¹H NMR (400 MHz, CDCl₃) δ 7.26 (m, 2H), 7.04 (t, J=8.6 Hz, 2H), 4.61 (s, 2H), 3.41 (d, J=6.8 Hz, 2H), 3.32 (d, J=2.8 Hz, 1H), 3.31 (s, 1H), 2.87 (dd, J=13.2; 4.2 Hz, 2H), 1.93 (m, 1H), 1.65 (m, 1H), 1.44 (s, 3H), 1.21 (s, 3H), 1.02 (m, 1H), 0.47 (m, 3H), 0.36 (m, 1H) ppm. ES MS M+1=373.

EXAMPLE 9

5-(Dimethylaminocarbonyl)-2-(4-fluorobenzyl)-8-hydroxy-6-methyl-2,3,4,4a,5,6-hexahydro-2,6-naphthyridine-1,7-dione

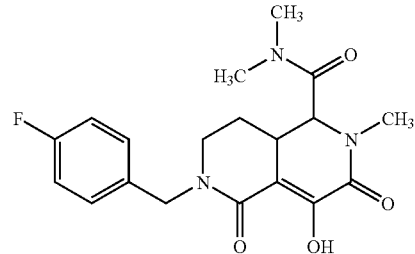

Step 1: 2-(4-Fluorobenzyl)-8-hydroxy-6-methyl-2,3,4,4a,5,6-hexahydro-2,6-naphthyridine-1,7-dione-5-carboxylic acid A solution of 5-(tert-butyloxycarbonyl)-2-(4-fluorobenzyl)-8-hydroxy-6-methyl-2,3,4,4a,5,6-hexahydro-2,6-naphthyridine-1,7-dione, Diastereomer 1 from Example 4, (0.015 g, 0.037 mmol) in 50% TFA in CH₂Cl₂ (2.4 mL) was stirred at room temperature. After 1.3 hours, TFA acid (0.5 mL) was added to the reaction mixture. After 48 hours, the reaction mixture was concentrated under vacuum to give the title compound. ES MS M+1=349.

Step 2: 5-(Dimethylaminocarbonyl)-2-(4-fluorobenzyl)-8-hydroxy-6-methyl-2,3,4,4a,5,6-hexahydro-2,6-naphthyridine-1,7-dione To a solution of 2-(4-fluorobenzyl)-8-hydroxy-6-methyl-2,3,4,4a,5,6-hexahydro-2,6-naphthyridine-1,7-dione-5-carboxylic acid (0.012 g, 0.0.034 mol) in DMF (0.5 mL) was added EDC (0.007 g, 0.038 mmol), dimethylamine hydrochloride (0.003 g, 0.038 mmol) and HOBT (0.006 g, 0.038 mmol). After stirring at room temperature, triethylamine (0.008 g, 0.076 mmol) was added. After 2 hours, the reaction mixture was concentrated under vacuum. The residual material was partitioned between $CHCl_3$ and water. The organic extract was dried with $Na_2SO_4$, filtered, and concentrated under vacuum. The residue was purified using reverse phase HPLC on a C18 stationary phase eluting with 15%-85% acetonitrile (0.1% TFA) in $H_2O$ (0.1% TFA) to provide the title compound. $^1$H NMR (400 MHz, $CDCl_3$) δ 7.25 (m, 2H), 7.04 (t, J=8.6 Hz, 2H), 4.75 (m, 1H), 4.44 (m, 1H), 3.95 (d, J=12.3 Hz, 1H), 3.29 (m, 4H), 3.18 (s, 3H), 1.81 (m, 1H), 1.65 (s, 6H), 1.49 (m, 1H) ppm. ES MS M+1=376.

EXAMPLES 10 TO 16

| Example | Compound | Data |
| --- | --- | --- |
| 10 | 2-(3-Chloro-4-fluorobenzyl)-8-hydroxy-5,5,6-trimethy-2,3,4,4a,5,6-hexahydro-2,6-naphthyridine-1,7-dione<br><br>The title compound was prepared using procedures analogous to Steps 1-3 of Example 1, with 3-chloro-4-fluorobenzyl bromide replacing 4-fluorobenzyl bromide, and then using procedures analogous to Steps 1-4 of Example 2.<br>The enantiomers of the title compound were separated with a ChiralPak AD column with 100% methanol as the mobile phase, wherein the first enantiomer had a retention time of 5.58 min and a negative sign of rotation, and the second enantiomer had a retention time of 7.67 min and a positive sign of rotation. | $^1$H NMR (400 MHz, $CDCl_3$) δ 7.32 (m, 1 H), 7.16 (m, 1 H), 7.12 (t, J = 8 Hz, 1 H), 4.64 (d, J = 16 Hz, 1 H), 4.52 (d, J = 16 Hz, 1 H), 3.34 (m, 2 H), 3.02 (s, 3 H), 2.84 (dd, J = 13.2; 4.2 Hz, 1 H), 2.46 (br, 1 H), 1.91 (m, 1 H), 1.65 (m, 1 H), 1.38 (s, 3 H), 1.14 (s, 3 H) ppm. ES MS M + 1 = 367. |
| 11 | 6'-(4-Fluorobenzyl)-4'-hydroxy-2'-methyl-6',7',8',8a'-tetrahydo-2'H-spiro[cyclopentane-1,1'-[2,6]-naphthyridine]-3',5'-dione<br><br>The title compound was prepared using procedures analogous to Example 2 except that nitrocyclopentane was used in Step 1 instead of 2-nitropropane.<br>The enantiomers of the title compound were separated using a ChiralPak AD column with 50% methanol in ethanol as the mobile phase, wherein the first enantiomer had a retention time of 5.05 min and a negative sign of rotation, and the second enantiomer had a retention time of 5.67 min and a positive sign of rotation. | $^1$H NMR (400 MHz, $CDCl_3$) δ 7.26 (m, 2 H), 7.04 (t, J = 8.7 Hz, 2 H), 4.67 (d, J = 14.5 Hz, 1 H), 4.52 (d, J = 14.6 Hz, 1 H), 3.29 (m, 2 H), 3.03 (s, 3 H), 2.93 (dd, J = 3.84; 13.2 Hz, 1 H), 2.22 (m, 3 H), 1.96 (m, 1 H), 1.82 (m, 1 H), 1.67 (m, 2 H), 1.45 (m, 1 H), 1.31 (m, 1 H) ppm. ES MS M + 1 = 359. |

| Example | Compound | Data |
|---|---|---|
| 12 | 2-(3,4-difluorobenzyl)-8-hydroxy-5,5,6-trimethy-2,3,4,4a,5,6-hexahydro-2,6-naphthyridine-1,7-dione 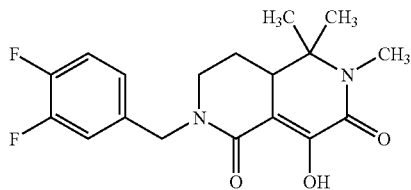 The title compound was prepared using procedures analogous to Steps 1-3 of Example 1, with 3,4-difluorobenzyl bromide replacing 4-fluorobenzyl bromide, and then using procedures analogous to Steps 1-4 of Example 2. | $^1$H NMR (400 MHz, CDCl$_3$) δ 7.13 (m, 2 H), 7.02 (m, 1 H), 4.66 (d, J = 16 Hz, 1 H), 4.49 (d, J = 16 Hz, 1 H), 3.34 (m, 2 H), 3.02 (s, 3 H), 2.84 (dd, J = 13, 4 Hz, 1 H), 1.93 (m, 1 H), 1.67 (m, 1 H), 1.39 (s, 3 H), 1.13 (s, 3 H) ppm. ES MS M + 1 = 351. |
| 13 | 6'-(4-Fluorobenzyl)-4'-hydroxy-2'-methyl-6',7',8',8a'-tetrahydro-2'H-spiro[cyclobutane-1,1'-[2,6]naphthyridine]-3',5'-dione 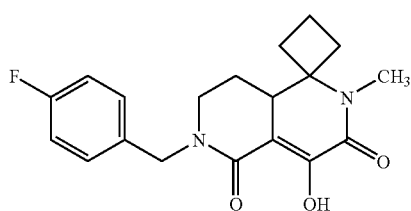 The title compound was prepared via Step 1 of Example 2 using nitrocyclobutane in place of 2-nitropropane, followed by Step 3 of Example 5, and then Steps 1 and 2 of Example 7. | $^1$H NMR (400 MHz, CDCl$_3$) δ 7.27 (m, 2 H), 7.05 (t, J = 8.4 Hz, 2 H), 4.69 (d, J = 14.5 Hz, 1 H), 4.54 (d, J = 14.7 Hz, 1 H), 3.41 (m, 2 H), 3.21 (s, 3 H), 2.84 (m, 2 H), 2.34 (m, 1 H), 2.22 (m, 1 H), 2.07 (m, 2 H), 1.94 (m, 2 H), 1.67 (m, 1 H) ppm. ES MS M + 1 = 345. |
| 14 | 5-[(2-Methylpropyl)aminocarbonyl]-2-(4-fluorobenzyl)-8-hydroxy-6-methyl-2,3,4,4a,5,6-hexahydro-2,6-naphthyridine-1,7-dione 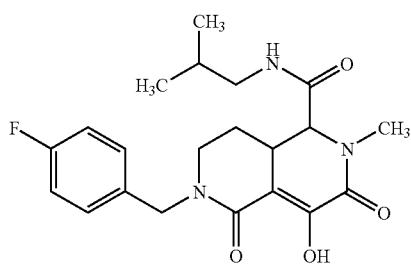 The title compound was prepared via a procedure analogous to Step 2 of Example 9, using the appropriate amine in place of dimethylamine hydrochloride. | $^1$H NMR (400 MHz, CD$_3$OD) δ 7.33 (m, 2 H), 7.07 (t, J = 8.8 Hz, 2 H), 4.73 (d, J = 14.6 Hz, 1 H), 4.51 (d, J = 14.6 Hz, 1 H), 3.92 (d, J = 12.4 Hz, 1 H), 3.40 (m, 1 H), 3.11 (m, 4 H), 2.93 (s, 3 H), 1.83 (m, 2 H), 1.61 (m, 1 H), 0.94 (s, 6 H) ppm. ES MS M + 1 = 404. |
| 15 | 5-(tert-Butylaminocarbonyl)-2-(4-fluorobenzyl)-8-hydroxy-6-methyl-2,3,4,4a,5,6-hexahydro-2,6-naphthyridine-1,7-dione 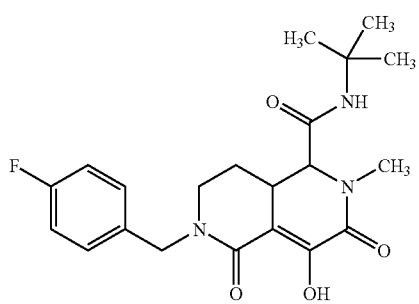 The title compound was prepared via a procedure analogous to Step 2 of Example 9, using the appropriate amine in place of dimethylamine hydrochloride. | ES MS M + 1 = 404. |

| Example | Compound | Data |
| --- | --- | --- |
| 16 | 5-[(2-Pyridylmethyl)aminocarbonyl]-2-(4-fluorobenzyl)-8-hydroxy-6-methyl-2,3,4,4a,5,6-hexahydro-2,6-naphthyridine-1,7-dione | ES MS M + 1 = 439. |

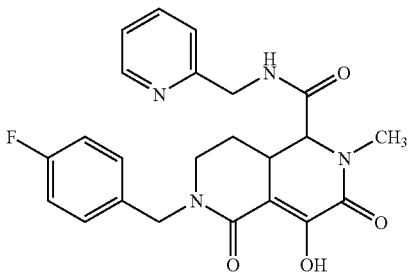

In the following two examples, this is HPLC Method A: Agilent Zorbax SB-C8 4.6 mm ID×75 mm 3.5 μm column with a 4.5 min linear gradient from 95:5 to 0:100 A:B (A=0.1% TFA in water, B=0.1% TFA in acetonitrile), flow rate=3 mL/min, UV detection at 215 nm.

EXAMPLE 17

5-(Pyrimidin-2-yl)-2-(4-fluorobenzyl)-8-hydroxy-6-methyl-2,3,4,4a,5,6-hexahydro-2,6-naphthyridine-1,7-dione

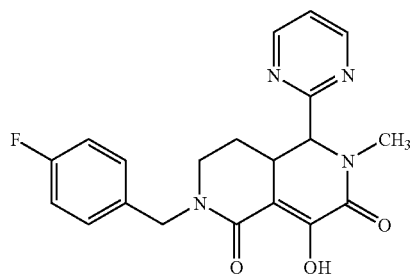

Step 1: Ethyl 2-oxo-2-[(pyrimidin-2-yl)methylamino]acetate

To a solution 2-aminomethylpyrimidine hydrochloride (0.96 g, 6.6 mmol) in dichloromethane (15 mL) was added DIEA (2.8 mL, 16.0 mmol). The mixture was cooled to 0° C. and ethyl oxalyl chloride (0.81 mL, 7.3 mmol) was added. After 15 min, the solvent was removed under reduced pressure and the residue was purified by pressurized silica gel column chromatography using a gradient of 0-5% MeOH in dichloromethane. The solvent was removed under reduced pressure from the fractions containing product to give the title compound as an oil. $^1$H NMR (400 MHz, DMSO-$d_6$) δ 9.34 (br t, 1H), 8.77 (d, J=5.0 Hz, 2H), 7.41 (t, J=5.0 Hz, 1H), 4.54 (d, J=6 Hz, 2H), 4.28 (q, J=7 Hz, 2H), 1.29 (t, J=7 Hz, 3H); HPLC RT=1.67 min (Method A); ES MS M+1=210.

Step 2: Ethyl 2-oxo-2-[N-methyl-N-(pyrimidin-2-yl)methylamino]acetate

A solution ethyl 2-oxo-2-[(pyrimidin-2-yl)methylamino]acetate from the previous step (1.0 g, 4.8 mmol) and iodomethane (0.5 mL, 8 mmol) in DMF (15 mL) was cooled to 0° C. and NaH (0.23 g of a 60% dispersion in mineral oil, 5.7 mmol) was added. The cooling bath was removed and the mixture was stirred at ambient temperature for 18 hours. Ethanol was added to quench the reaction and the solvent was removed under reduced pressure. The residue was purified by pressurized silica gel column chromatography using a gradient of 80-100% EtOAc in hexanes. The solvent was removed under reduced pressure from the fractions containing product to give the title compound as an oil. $^1$H NMR (400 MHz, DMSO-$d_6$) δ 8.81 (m, 2H), 7.45 (m, 1H), 4.74 (m, 2H), 4.32, 4.13 (two q, rotamers, J=7 Hz, 2H), 3.08, 3.00 (two s, rotamers, 3H), 1.30, 1.08 (two t, rotamers, 3H); ES MS M+1=224.

Step 3: 5-(Pyrimidin-2-yl)-2-(4-fluorobenzyl)-8-hydroxy-6-methyl-2,3,4,4a,5,6-hexahydro-2,6-naphthyridine-1,7-dione To a cooled (−78° C.) solution of ethyl 2-oxo-2-[N-methyl-N-(pyrimidin-2-yl)methylamino]acetate from the previous step (1.43 g, 5.85 mmol) and 1-(3-chloro-4-fluorobenzyl)-5,6-dihydropyridin-2(1H)-one (1 g, 5 mmol) in anhydrous THF (10 mL) was added LiHMDS (1 M in THF) (1.02 g, 6.09 mmol) dropwise. The reaction mixture was stirred for 10 min at −78° C., warmed to room temperature for 2.5 hours, then heated to 40° C. for 48 hours. The mixture was cooled to ambient temperature and the solvent was removed under vacuum. The residual material was purified using reverse phase HPLC on a C18 stationary phase eluting with 5%-95% acetonitrile (0.1% TFA) in $H_2O$ (0.1% TFA) to give the title compound as a mixture of enantiomers. The hydrogens at positions 4a and 5 were found to have a trans relationship to one another. The enantiomers were separated on a ChiralPak AD column with 1:1 EtOH:MeOH as the mobile phase. The first eluting enantiomer had a positive sign of rotation and the following properties: $^1$H NMR (400 MHz, $CD_3OD$), δ8.76 (d, J=4.8 Hz, 2H), 7.41 (t, J=4.8 Hz, 1H), 7.23 (dd, J=8.5, 5.5 Hz, 2H), 7.01 (t, J=Hz, 2H), 4.81 (d, J=6.7 Hz, 1H), 4.57 (d, J=15 Hz, 1H), 4.47 (d, J=15 Hz, 1H), 3.63 (m, 1H), 3.2-3.4 (m, 2H), 2.91 (s, 3H), 2.11 (m, 1H), 0.96 (dq, Jd=4.5 Hz, Jq=13 Hz, 1H). ES MS M+1=383. The second eluting enantiomer had a negative sign of rotation and $^1$H NMR and MS properties identical to that of the first eluting enantiomer.

EXAMPLE 18

2-(3-Chloro-4-fluorobenzyl)-8-hydroxy-6-cyclopropyl-2,3,4,4a,5,6-hexahydro-2,6-naphthyridine-1,7-dione

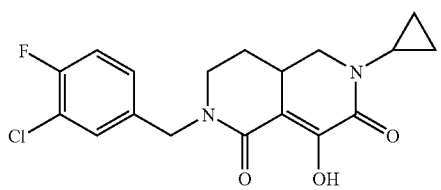

Step 1: 1-(3-Chloro-4-fluorobenzyl)-4-cyano-5,6-dihydropyridin-2(1H)-one

A suspension of 1-(3-chloro-4-fluorobenzyl)-5,6-dihydropyridin-2(1H)-one (10 g, 42 mmol) and KCN (8:0 g, 120 mmol) in DMF (400 mL) and water (100 mL) was warmed to 90° C. for 48 hours. The solvents were removed under reduced pressure and the residue was partitioned between EtOAc (250 mL) and water (100 mL). The organic phase was separated and the aqueous phase was extracted with more EtOAc (2×100 mL). The organic phases were combined and the solvent was removed under reduced pressure. The residue was purified by pressurized silica gel column chromatography eluting with 2:1:0.01 EtOAc:hexanes:MeOH. Fractions containing product were concentrated under reduced pressure to give the title compound as a solid. $^1$H NMR (400 MHz, CDCl$_3$) δ 7.32 (dd, J=6.8, 2.0 Hz, 1H), 7.1-7.2 (m, 2H), 4.55 (AB quartet, J=17 Hz, 2H), 3.46 (ddd, J=13, 7.1, 6.5 Hz, 1H); 3.28 (ddd, J=13, 7.1, 6.5 Hz, 1H), 3.10 (m, 1H), 2.78 (ABX, J 17, 6.4 Hz, 2H), 2.2-2.2 (m, 2H); HPLC RT=2.36 min (Method A); ES MS M+1=267.

Step 2: Methyl 1-(3-chloro-4-fluorobenzyl)-5,6-dihydropyridin-2(1H)-one-4-carboxylate HCl gas was bubbled through a solution of 1-(3-Chloro-4-fluorobenzyl)-4-cyano-5,6-dihydropyridin-2(1H)-one (4.5 g, 59 mmol) from the previous step chilled to 0° C. in methanol (75 mL). After 10 min, the HCl source was removed, and the stirred mixture was allowed to warm to ambient temperature for 3 hours. The solvent was removed under reduced pressure and the residue was purified by pressurized silica gel column chromatography eluting with 97:3 CH$_2$Cl$_2$:MeOH. Fractions containing product were concentrated under reduced pressure to give the title compound as a gum. HPLC RT=3.03 min (Method A); ES MS M+1=300.

Step 3: 1-(3-Chloro-4-fluorobenzyl)-4-hydroxymethyl-5,6-dihydropyridin-2(1H)-one A solution of methyl 1-(3-chloro-4-fluorobenzyl)-5,6-dihydropyridin-2(1H)-one-4-carboxylate (4.0 g, 13 mmol) from the previous step in THF (75 mL) was cooled to −78° C. with stirring. A solution of lithium borohydride in THF (15 mL of a 2.0 M solution, 30 mmol) was added and the mixture was stirred at −78° C. for 30 min and then at ambient temperature for 24 hours. The reaction was quenched by the careful addition of 1 N aqueous HCl. Enough HCl was added so that the solution measured pH 1. The solvent was removed under reduced pressure and the residue was partitioned between CH$_2$Cl$_2$ (100 mL) and water (50 mL). The organic layer was separated and the aqueous phase was extracted with more CH$_2$Cl$_2$ (2×100 mL). The organic phases were combined and the solvent was removed under reduced pressure. The residue was purified by pressurized silica gel column chromatography eluting with 95:5 CH$_2$Cl$_2$:MeOH. Fractions containing product were concentrated under reduced pressure to give the title compound as a gum. HPLC RT=2.67 min (Method A); ES MS M+1=272.

Step 4: 1-(3-Chloro-4-fluorobenzyl)-4-methylsulfonyloxymethyl-5,6-dihydropyridin-2(1H)-one A solution of 1-(3-chloro-4-fluorobenzyl)-4-hydroxymethyl-5,6-dihydropyridin-2(1H)-one (3.1 g, 11 mmol) from the previous step and DIEA (2.8 mL, 16 mmol) in CH$_2$Cl$_2$ (50 mL) was cooled to 0° C. with stirring. Methanesulfonyl chloride (1.4 g, 12 mmol) was added and the mixture was stirred at 0° C. for 30 min and then at ambient temperature for 1 hour. The reaction mixture was diluted with CH$_2$Cl$_2$ (75 mL) and extracted with water (2×30 mL). The CH$_2$Cl$_2$ layer was dried (MgSO$_4$), filtered, and the solvent was removed under reduced pressure to give the title compound as a gum. $^1$H NMR (400 MHz, CDCl$_3$) δ 7.31 (dd, J=6.9, 2.9 Hz, 1H), 7.1-7.2 (m, 2H), 4.64 (d, J=15 Hz, 1H), 4.44 (d, J=15 Hz, 1H), 4.13 (ABX, J=6, 15 Hz, 2H), 3.28 (m, 2H), 3.04 (s, 3H), 2.64 (m, 1H), 2.34 (m, 1H), 2.23 (dd, J=6, 16 Hz, 1H), 2.02 (m, 1H), 1.61 (m, 1H); HPLC RT=2.99 min (Method A); ES MS M+1=350.

Step 5: 1-(3-Chloro-4-fluorobenzyl)-4-cyclopropylaminomethyl-5,6-dihydropyridin-2(H)-one 1-(3-Chloro-4-fluorobenzyl)-4-methylsulfonyloxymethyl-5,6-dihydropyridin-2(H)-one (2.0 g, 5.7 mmol) from the previous step was dissolved in cyclopropylamine (10 mL) and the mixture was heated to 60° C. with stirring in a sealed vessel for 18 hours. The excess cyclopropyl amine was removed under reduced pressure and the residue was partitioned between CH$_2$Cl$_2$ (75 mL) and saturated aqueous NaHCO$_3$ (30 mL). The CH$_2$Cl$_2$ layer was collected and aqueous phase was extracted with more CH$_2$Cl$_2$ (2×50 mL). The organic phases were combined and the solvent was removed under reduced pressure. The residue was purified by pressurized silica gel column chromatography eluting with 95:5 CH$_2$Cl$_2$:MeOH. Fractions containing product were concentrated under reduced pressure to give the title compound as a gum. $^1$H NMR (400 MHz, solvent) δ 7.29 (dd, J=7, 2 Hz, 1H), 7.15-7.25 (m, 2H), 4.65 (d, J=15 Hz, 1H), 4.29 (d, J=15 Hz, 1H), 3.21 (m, 2H), 2.45-2.7 (m, 3H), 2.05-2.15 (m, 2H), 2.0 (m, 1H), 1.45 (m, 1H), 0.78 (m, 1H), 0.42 (m, 2H), 0.29 (m, 2H); HPLC RT=2.45 min (Method A); ES MS M+1=311.

Step 6: 1-(3-Chloro-4-fluorobenzyl)-4-(N-(methyl oxalyl)-N-cyclopropylaminomethyl)-5,6-dihydropyridin-2(1H)-one To a stirred solution of 1-(3-chloro-4-fluorobenzyl)-4-cyclopropylaminomethyl-5,6-dihydropyridin-2(1H)-one (1.0 g, 3.2 mmol) from the previous step and DIEA (0.87 mL, 5.0 mmol) in CH$_2$Cl$_2$ (20 mL) cooled to 0° C. and methyl oxalyl chloride (0.47 g, 3.8 mmol) was added. The mixture was stirred for 30 min at 0° C., then warmed to ambient temperature and stirred for 1 hour. The reaction was diluted with CH$_2$Cl$_2$ (30 mL) and water (20 mL) was added. The CH$_2$Cl$_2$ layer was collected and the solvent was removed under reduced pressure. The residue was purified by pressurized silica gel column chromatography eluting with EtOAc. Fractions containing product were concentrated under reduced pressure to give the title compound as a gum. HPLC RT=3.18 min (Method A); ES MS M+1=397.

Step 7: 2-(3-Chloro-4-fluorobenzyl)-8-hydroxy-6-cyclopropyl-2,3,4,4a,5,6-hexahydro-2,6-naphthyridine-1,7-dione To a stirred solution of diisopropylamine (0.59 mL, 4.2 mmol) in THF (10 mL) at 0° C. was added n-butyllithium (1.4 mL of a 2.5 M solution in hexanes, 3.5 mmol). The mixture was stirred at 0° C. for 5 min to generate LDA and then cooled to −78° C. A stirred solution of 1-(3-chloro-4-fluorobenzyl)-4-(N-(methyl oxalyl)-N-cyclopropylaminomethyl)-5,6-dihydropyridin-2(1H)-one (1.1 g, 2.8 mmol) from the previous step in THF (15 mL) was cooled to −78° C. To this solution was slowly added the cold solution of LDA via cannula. The mixture was stirred at −78° C. for 10 min, then the cooling bath was removed and the mixture was allowed to warm to ambient temperature and stirred for 18. The reaction was quenched by the addition of acetic acid (1 mL), and the solvent was removed under reduced pressure. The residue was purified by preparative reverse phase HPLC using a water:acetonitrile gradient containing 0.1% TFA. Fractions containing product were concentrated under reduced pressure to give the title compound as a mixture of enantiomers. $^1$H NMR (400 MHz, CDCl$_3$) δ 7.31 (dd, J=7, 2 Hz, 1H), 7.1-7.2 (m, 2H), 4.69 (d, J=15 Hz, 1H), 4.45 (d, J=15 Hz, 1H), 3.2-3.4 (m, 3H), 2.96 (m, 1H), 2.81 (septet, J=6 Hz, 1H), 1.94 (m, 1H), 1.57 (dq, Jd=6 Hz, Jq=15 Hz, 1H), 0.96 (m, 1H), 0.75-0.85 (m, 2H), 0.65 (1H); HPLC RT=3.24 min (Method A); ES MS M+1=365. The enantiomers were separated on a chiral stationary phase (ChiralPak AD) using 60:20:20 hexanes:methanol:ethanol containing 0.1% diethylamine as the mobile phase. On an analytical ChiralPak AD column, the first eluting enantiomer had a retention time of 7.3 min and a negative sign of rotation, the second eluting enantiomer had a retention time of 8.4 min and a positive sign of rotation.

EXAMPLE 19

Oral Compositions

As a specific embodiment of an oral composition of a compound of this invention, 50 mg of compound of Example 1 is formulated with sufficient finely divided lactose to provide a total amount of 580 to 590 mg to fill a size 0 hard gelatin capsule. Encapsulated oral compositions containing any one of the compounds of Examples 2-18 can be similarly prepared.

EXAMPLE 20

HIV Integrase Assay: Strand Transfer Catalyzed by Recombinant Integrase

Assays for the strand transfer activity of integrase were conducted in accordance with WO 02/30930 for recombinant integrase. Representative compounds of the present invention exhibit inhibition of strand transfer activity in this assay. For example, the compounds prepared in Examples 1-18 were tested in the integrase assay, and the compounds of Examples 1-16, Example 18, and the first eluting enantiomer of Example 17 were found to have IC$_{50}$ values of about 1 micromolar or less.

Further description on conducting the assay using preassembled complexes is found in Wolfe, A. L. et al., *J. Virol.*
1996, 70: 1424-1432, Hazuda et al., *J. Virol.* 1997, 71: 7005-7011; Hazuda et al., *Drug Design and Discovery* 1997, 15: 17-24; and Hazuda et al., *Science* 2000, 287: 646-650.

EXAMPLE 21

Assay for Inhibition of HIV Replication

Assays for the inhibition of acute HIV infection of T-lymphoid cells were conducted in accordance with Vacca, J. P. et al., *Proc. Natl. Acad. Sci. USA* 1994, 91: 4096. Representative compounds of the present invention exhibit inhibition of HIV replication in this assay. For example, the compounds prepared in Examples 1-18 all tested in the inhibition assay, and the compounds of Examples 1-16, Example 18, and the first eluting enantiomer of Example 17 were found to have IC$_{95}$ values of about 10 micromolar or less.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of Formula I, or an individual enantiomer or diastereomer thereof, or a pharmaceutically acceptable salt thereof:

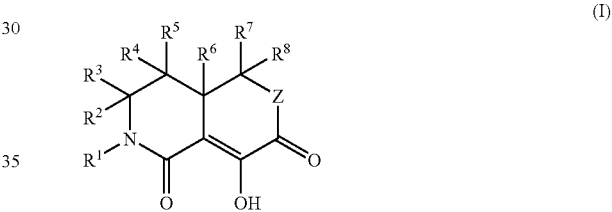

wherein:
  Z is N—R$^9$;
  R$^1$ is —CH$_2$—R$^J$, and R$^J$ is phenyl which is optionally substituted with from 1 to 4 substituents each of which is independently:
    (1) —C$_{1-4}$ alkyl,
    (2) —O—C$_{1-4}$ alkyl,
    (3) —C$_{1-4}$ haloalkyl,
    (4) —O—C$_{1-4}$ haloalkyl,
    (5) halo,
    (6) —CN,
    (7) —N(R$^A$)R$^B$,
    (8) —C(=O)N(R$^A$)R$^B$,
    (9) —S(=O)R$^A$,
    (10) —SO$_2$R$^A$,
    (11) —N(R$^A$)SO$_2$R$^B$,
    (12) —N(R$^A$)SO$_2$N(R$^A$)R$^B$,
    (13) —N(R$^A$)C(=O)R$^B$, or
    (14) —N(R$^A$)C(=O)—C(=O)N(R$^A$)R$^B$;
  R$^2$ and R$^4$ are each independently:
    (1) —H,
    (2) —C$_{1-6}$ alkyl, which is optionally substituted with —OH, —O—C$_{1-6}$ alkyl, —O—C$_{1-6}$ haloalkyl, —CN, —N(R$^A$)R$^B$, —C(=O)N(R$^A$)R$^B$, —C(=O)R$^A$, —CO$_2$R$^A$, —S(O)$_n$R$^A$, —SO$_2$N(R$^A$)R$^B$, —N(R$^A$)C(=O)R$^B$, —N(R$^A$)CO$_2$R$^B$, —N(R$^A$)SO$_2$R$^B$, —N(R$^A$)SO$_2$N(R$^A$)R$^B$, —N(R$^A$)C(=O)N(R$^A$)R$^B$, or —OC(=O)N(R$^A$)R$^B$, (3) —$C_{1-6}$ haloalkyl,
(4) CycA,
(5) AryA,
(6) HetC, or
(7) —$C_{1-6}$ alkyl substituted with CycA, AryA, or HetC;

$R^3$ and $R^5$ are both H;

$R^6$ is:
(1) —H,
(2) —$C_{1-6}$ alkyl,
(3) —$C_{1-6}$ fluoroalkyl,
(4) CycA,
(5) AryA, or
(6) —$C_{1-6}$ alkyl substituted with AryA;

$R^7$ is H or —$C_{1-6}$ alkyl;

$R^8$ is:
(1) —H,
(2) —$C_{1-6}$ alkyl,
(3) —$CO_2R^A$,
(4) —C(=O)N($R^A$)$R^B$,
(5) —$R^K$,
(6) —C(=O)—$R^K$,
(7) —C(=O)N($R^A$)—$R^K$, or
(8) —C(=O)N($R^A$)—$C_{1-6}$ alkylene-$R^K$;

or alternatively $R^7$ and $R^8$ together with the carbon atom to which they are both attached form a 3- to 7-membered saturated carbocyclic ring;

$R^9$ is:
(1) —H,
(2) —$C_{1-6}$ alkyl,
(3) —$C_{1-6}$ fluoroalkyl,
(4) CycA, or
(5) —$C_{1-6}$ alkyl substituted with CycA, AryA, or HetC;

each n is independently an integer equal to zero, 1, or 2;
each $R^A$ is independently H or $C_{1-6}$ alkyl;
each $R^B$ is independently H or $C_{1-6}$ alkyl;
each $R^K$ is independently CycA, AryA, or HetC;
each CycA is independently a $C_{3-8}$ cycloalkyl, which is optionally substituted with from 1 to 4 substituents each of which is halogen, —OH, —$C_{1-6}$ alkyl, —$C_{1-6}$ haloalkyl, —O—$C_{1-6}$ alkyl, or —O—$C_{1-6}$ haloalkyl;
each AryA is independently phenyl, which is optionally substituted with from 1 to 5 substituents each of which is independently —$C_{1-6}$ alkyl, —$C_{1-6}$ alkylene-OH, —$C_{1-6}$ alkylene-O—$C_{1-6}$ alkyl, —$C_{1-6}$ alkylene-O—$C_{1-6}$ haloalkyl, —$C_{1-6}$ alkylene-N($R^A$)$R^B$, —$C_{1-6}$ alkylene-C(=O)N($R^A$)$R^B$, —$C_{1-6}$ alkylene-C(=O)$R^A$, —$C_{1-6}$ alkylene-$CO_2R^A$, —$C_{1-6}$ alkylene-S(O)$_n$$R^A$, —O—$C_{1-6}$ alkyl, —$C_{1-6}$ haloalkyl, —O—$C_{1-6}$ haloalkyl, —OH, halo, —N($R^A$)$R^B$, —C(=O)N($R^A$)$R^B$, —C(=O)$R^A$, —$CO_2R^A$, —S(O)$_n$$R^A$, or —$SO_2$N($R^A$)$R^B$; and
each HetC is independently a saturated or unsaturated heterocyclic ring which is:
(i) a saturated heterocyclic ring selected from the group consisting of piperidinyl, morpholinyl, thiomorpholinyl, thiazolidinyl, isothiazolidinyl, oxazolidinyl, isoxazolidinyl, pyrrolidinyl, azetidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl, and dioxanyl,
(ii) a mono-unsaturated heterocyclic ring selected from mono-unsaturated counterparts of the saturated rings in (i), or
(iii) an aromatic heterocyclic ring selected from the group consisting of pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl,
wherein the heterocyclic ring is optionally substituted with from 1 to 4 substituents each of which is halogen, —$C_{1-6}$ alkyl, —$C_{1-6}$ haloalkyl, —O—$C_{1-6}$ alkyl, —O—$C_{1-6}$ haloalkyl, OH, or oxo.

2. The compound according to claim 1, or an individual enantiomer or diastereomer thereof, or a pharmaceutically acceptable salt thereof, wherein $R^6$ is H.

3. A compound according to claim 1, which is a compound of Formula IIa, or an individual enantiomer or diastereomer thereof, or a pharmaceutically acceptable salt thereof:

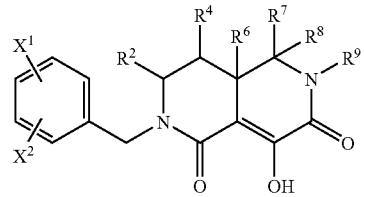

(IIa)

wherein:

$X^1$ and $X^2$ are each independently —H, —$C_{1-4}$ alkyl, —O—$C_{1-4}$ alkyl, —$C_{1-4}$ haloalkyl, —O—$C_{1-4}$ haloalkyl, halo, —CN, —N($R^A$)$R^B$, —C(=O)N($R^A$)$R^B$, or —S(O)$_n$$R^A$;

$R^2$ and $R^4$ are each independently —H, —$C_{1-4}$ alkyl, —$C_{1-4}$ fluoroalkyl, $C_{3-6}$ cycloalkyl, phenyl, or benzyl;

$R^6$ is H, —$C_{1-4}$ alkyl, —$CF_3$, cyclopropyl, phenyl or benzyl;

$R^7$ is H or —$C_{1-4}$ alkyl;

$R^8$ is —H, —$C_{1-4}$ alkyl, —$CO_2$—$C_{1-4}$ alkyl, —C(=)NH($C_{1-4}$ alkyl), —C(=O)N($C_{1-4}$ alkyl)$_2$, $C_{3-6}$ cycloalkyl, HetE, —C(=O)-HetE, or —C(=O)N($R^A$)—(CH$_2$)$_{1-2}$-HetF; wherein HetE is a saturated heterocyclic ring selected from the group consisting of piperidinyl, morpholinyl, thiomorpholinyl, thiazolidinyl, isothiazolidinyl, oxazolidinyl, isoxazolidinyl, pyrrolidinyl, azetidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl and dioxanyl, wherein the saturated heterocyclic is optionally substituted with from 1 to 3 substituents each of which is independently oxo or $C_{1-4}$ alkyl; and with the proviso that the saturated heterocyclic is attached to the —C(=O)— via a ring N atom; and HetF is a heteroaromatic ring selected from the group consisting of pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl and thiadiazolyl, wherein the heteroaromatic ring is optionally substituted with 1 or 2 substituents each of which is independently a $C_{1-4}$ alkyl;

or alternatively $R^7$ and $R^8$ together with the carbon atom to which they are both attached form a 3- to 6-membered saturated carbocyclic ring;

R⁹ is —H, —C₁₋₄ alkyl, —CH₂CF₃, —C₃₋₆ cycloalkyl, —CH₂—C₃₋₆ cycloalkyl, or —CH₂-phenyl;
each $R^A$ is independently H or C₁₋₄ alkyl; and
each $R^B$ is independently H or C₁₋₄ alkyl.

4. A compound according to claim 3, or an individual enantiomer or diastereomer thereof, or a pharmaceutically acceptable salt thereof, wherein:
 $X^1$ and $X^2$ are each independently H, fluoro, chloro, methyl, trifluoromethyl, methoxy, CN, —SO₂CH₃, —C(=O)NH(CH₃), or —C(=O)N(CH₃)₂;
 $R^2$ and $R^4$ are both H;
 $R^6$ is H, methyl, cyclopropyl, or phenyl;
 $R^7$ is H or methyl;
 $R^8$ is —H, —C₁₋₄ alkyl, —CO₂—C₁₋₄ alkyl, —C(=O)NH(C₁₋₄ alkyl), —C(=O)N(C₁₋₄ alkyl)₂, C₃₋₆ cycloalkyl, HetF, —C(=O)-HetE, or —C(=O)N($R^A$)—(CH₂)₁₋₂-HetF; wherein
 HetE is selected from the group consisting of:

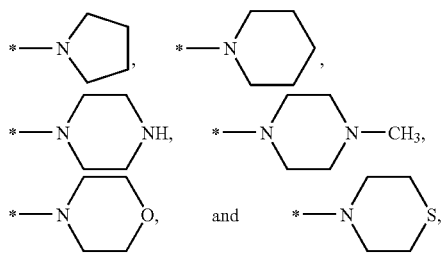

wherein the asterisk * denotes the point of attachment to the —C(=O) moiety; and
HetF is selected from the group consisting of pyrrolyl, imidazolyl, triazolyl, tetrazolyl, oxazolyl, isooxazolyl, pyridyl, pyrimidinyl, and pyrazinyl;
or alternatively $R^7$ and $R^8$ together with the carbon atom to which they are both attached form cyclopropyl, cyclobutyl, cyclopentyl, or cyclohexyl; and
 $R^9$ is H, methyl, ethyl, n-propyl, isopropyl, —CH₂CF₃, cyclopropyl, or —CH₂-cyclopropyl.

5. A compound, according to claim 1, or a pharmaceutically acceptable salt thereof, selected from the group consisting of:
 2-(4-fluorobenzyl)-8-hydroxy-6-methyl-2,3,4,4a,5,6-hexahydro-2,6-naphthyridine-1,7-dione;
 2-(4-fluorobenzyl)-8-hydroxy-5,5,6-trimethyl-2,3,4,4a,5,6-hexahydro-2,6-naphthyridine-1,7-dione;
 (+)-2-(4-fluorobenzyl)-8-hydroxy-5,5,6-trimethyl-2,3,4,4a,5,6-hexahydro-2,6-naphthyridine-1,7-dione;
 (−)-2-(4-fluorobenzyl)-8-hydroxy-5,5,6-trimethyl-2,3,4,4a,5,6-hexahydro-2,6-naphthyridine-1,7-dione;
 2-(4-fluorobenzyl)-8-hydroxy-6-methyl-4a-phenyl-2,3,4,4a,5,6-hexahydro-2,6-naphthyridine-1,7-dione;
 (+)-2-(4-fluorobenzyl)-8-hydroxy-6-methyl-4a-phenyl-2,3,4,4a,5,6-hexahydro-2,6-naphthyridine-1,7-dione;
 (−)-2-(4-fluorobenzyl)-8-hydroxy-6-methyl-4a-phenyl-2,3,4,4a,5,6-hexahydro-2,6-naphthyridine-1,7-dione;
 5-(tert-butyloxycarbonyl)-2-(4-fluorobenzyl)-8-hydroxy-6-methyl-2,3,4,4a,5,6-hexahydro-2,6-naphthyridine-1,7-dione, and diastereomers and enantiomers thereof;
 5-ethyl-2-(4-fluorobenzyl)-8-hydroxy-6-methyl-2,3,4,4a,5,6-hexahydro-2,6-naphthyridine-1,7-dione, and diastereomers and enantiomers thereof;
 6-(cyclopropylmethyl)-2-(4-fluorobenzyl)-8-hydroxy-5,5-dimethyl-2,3,4,4a,5,6-hexahydro-2,6-naphthyridine-1,7-dione;
 5-(dimethylaminocarbonyl)-2-(4-fluorobenzyl)-8-hydroxy-6-methyl-2,3,4,4a,5,6-hexahydro-2,6-naphthyridine-1,7-dione, and diastereomers and enantiomers thereof
 2-(3-chloro-4-fluorobenzyl)-8-hydroxy-5,5,6-trimethyl-2,3,4,4a,5,6-hexahydro-2,6-naphthyridine-1,7-dione;
 (+)-2-(3-chloro-4-fluorobenzyl)-8-hydroxy-5,5,6-trimethyl-2,3,4,4a,5,6-hexahydro-2,6-naphthyridine-1,7-dione;
 (−)-2-(3-chloro-4-fluorobenzyl)-8-hydroxy-5,5,6-trimethyl-2,3,4,4a,5,6-hexahydro-2,6-naphthyridine-1,7-dione;
 6'-(4-fluorobenzyl)-4'-hydroxy-2'-methyl-6',7',8',8a'-tetrahydro-2' H-spiro[cyclopentane-1,1'-[2,6]naphthyridine]-3',5'-dione;
 (+)-6'-(4-fluorobenzyl)-4'-hydroxy-2'-methyl-6',7',8',8a'-tetrahydro-2' H-spiro[cyclopentane-1,1'-[2,6]naphthyridine]-3',5'-dione;
 (−)-6'-(4-fluorobenzyl)-4'-hydroxy-2'-methyl-6',7',8',8a'-tetrahydro-2' H-spiro[cyclopentane-1,1'-[2,6]naphthyridine]-3',5'-dione;
 2-(3,4-difluorobenzyl)-8-hydroxy-5,5,6-trimethyl-2,3,4,4a,5,6-hexahydro-2,6-naphthyridine-1,7-dione;
 6'-(4-fluorobenzyl)-4'-hydroxy-2'-methyl-6',7',8',8a'-tetrahydro-2' H-spiro[cyclobutane-1,1'-[2,6]naphthyridine]-3',5'-dione;
 5-[(2-methylpropyl)aminocarbonyl]-2-(4-fluorobenzyl)-8-hydroxy-6-methyl-2,3,4,4a,5,6-hexahydro-2,6-naphthyridine-1,7-dione, and diastereomers and enantiomers thereof;
 5-(tert-butylaminocarbonyl)-2-(4-fluorobenzyl)-8-hydroxy-6-methyl-2,3,4,4a,5,6-hexahydro-2,6-naphthyridine-1,7-dione, and diastereomers and enantiomers thereof;
 5-[(2-pyridylmethyl)aminocarbonyl]-2-(4-fluorobenzyl)-8-hydroxy-6-methyl-2,3,4,4a,5,6-hexahydro-2,6-naphthyridine-1,7-dione, and diastereomers and enantiomers thereof
 5-(pyrimidin-2-yl)-2-(4-fluorobenzyl)-8-hydroxy-6-methyl-2,3,4,4a,5,6-hexahydro-2,6-naphthyridine-1,7-dione, and diastereomers and enantiomers thereof;
 2-(3-chloro-4-fluorobenzyl)-8-hydroxy-6-cyclopropyl-2,3,4,4a,5,6-hexahydro-2,6-naphthyridine-1,7-dione;
 (+)-2-(3-chloro-4-fluorobenzyl)-8-hydroxy-6-cyclopropyl-2,3,4,4a,5,6-hexahydro-2,6-naphthyridine-1,7-dione; and
 (−)-2-(3-chloro-4-fluorobenzyl)-8-hydroxy-6-cyclopropyl-2,3,4,4a,5,6-hexahydro-2,6-naphthyridine-1,7-dione.

6. A pharmaceutical composition comprising a compound according to claim 1, or an individual enantiomer or diastereomer thereof, or a pharmaceutically acceptable salt thereof, and a pharmaceutically acceptable carrier.

* * * * *